(12) United States Patent
Öhrlein et al.

(10) Patent No.: US 7,855,302 B2
(45) Date of Patent: Dec. 21, 2010

(54) PROCESS FOR THE PREPARATION OF INTERMEDIATES USEFUL IN THE SYNTHESIS OF STATIN DERIVATIVES ESPECIALLY 7-AMINO-3,5-DIHYDROXYHEPANOIC ACID DERIVATIVES AND INTERMEDIATES THEREOF

(75) Inventors: Reinhold Öhrlein, Rheinfelden-Herten (DE); Gabriele Baisch, Binzen (DE); Nicole End, Oberwil (CH); Stephan Burkhardt, Gelterkinden (CH); Martin Studer, Basel (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 12/220,390

(22) Filed: Jul. 24, 2008

(65) Prior Publication Data
US 2008/0312466 A1    Dec. 18, 2008

Related U.S. Application Data

(62) Division of application No. 10/482,463, filed as application No. PCT/EP02/07307 on Jul. 2, 2002, now Pat. No. 7,420,078.

(30) Foreign Application Priority Data

Jul. 6, 2001   (EP) .................................. 01810670

(51) Int. Cl.
C07C 69/66 (2006.01)
C07C 259/06 (2006.01)
C07C 69/22 (2006.01)

(52) U.S. Cl. .................. 560/155; 560/184; 560/231

(58) Field of Classification Search ................. 560/155, 560/184, 231
See application file for complete search history.

(56) References Cited

U.S. PATENT DOCUMENTS

| | | | |
|---|---|---|---|
| 4,677,211 A | 6/1987 | Jewell, Jr. et al. | 548/491 |
| 4,950,775 A | 8/1990 | Heathcock et al. | 550/438 |
| 5,432,199 A * | 7/1995 | Cavazza | 514/546 |
| 5,599,954 A | 2/1997 | Mitsuhashi et al. | 549/419 |
| 2003/0166946 A1 | 9/2003 | Wolleb et al. | 548/494 |
| 2008/0312466 A1 | 12/2008 | Ohrlein et al. | |

FOREIGN PATENT DOCUMENTS

| | | |
|---|---|---|
| EP | 0352864 | 1/1990 |
| EP | 0436851 | 7/1991 |
| WO | 93/07115 | 4/1993 |
| WO | 03/004455 | 1/2003 |
| WO | 03/004456 | 1/2003 |

OTHER PUBLICATIONS

Gopalan et al. "Bifunctional Chiral Synthons Via Biochemical Methods. 5. Preparation of (S)-Ethyl Hydrogen-3-Hydroxyglutarate, Key Intermediate to (r)-4-amino-3-hydroxybutyric acid and L-carnitine" Tetrahedron Letters 1984, vol. 25, No. 46, pp. 5235-5238.*

D. W. Brooks et al, Tetrahedron Letters, vol. 25, No. 41, pp. 4623-4626, (1984).

R. Roy et al., Tetrahedron Letters, vol. 28, No. 42, pp. 4935-4938, (1987).

Beilstein Registry No. 1726574, Reaction 3/5, R-enantiomer, abstract, J. Org. Chem., vol. 53, No. 7, (1988), pp. 1567-1569.

Beilstein Registry No. 3544747, Reaction 3/5, abstract, Synth. Commun., vol. 20, No. 3, (1990), pp. 315-319.

P. Theisen et al., J. Org. Chem. vol. 53, (1988), pp. 2374-2378.

C. Heathcock et al., J. Med. Chem., vol. 30, (1987), pp. 1858-1873.

C. Blackwell et al., J. Org. Chem., vol. 57, (1992), pp. 1935-1937.

Beilstein Registry No. 7019202, abstract, Tetrahedron Lett., vol. 36, No. 1, (1995), pp. 43-46.

Beilstein Registry No. 4691462, abstract, Tetrahedron Lett., vol. 28, No. 4, (1987), pp. 391-394.

Chem. Abstr. 120:54803 for Journal of Organic Chemistry (1993), vol. 58, (25), pp. 7185-7194.

Chem. Abstr. 107:175723 for J. Chem. Soc., Perkin Trans. 1 (1987), (1), pp. 131-135.

Chem. Abstr. 117:47869 for Tetrahedron Letters (1992), vol. 33, (18), pp. 2455-2458.

Chem. Abstr. vol. 121, No. 11, (1994), abstract No. 134224b for Synth. Commun. (1994), vol. 24, (13), pp. 1833-1845.

(Continued)

*Primary Examiner*—Joseph R Kosack
(74) *Attorney, Agent, or Firm*—Tyler A. Stevenson

(57) ABSTRACT

The invention relates to novel synthesis methods for the preparation of statin derivatives, which methods proceed by way of a key intermediate of formula I

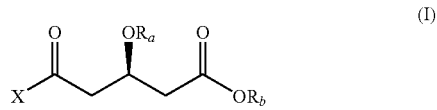

(I)

wherein X is halogen, acyloxy, activated hydrocarbyloxy, activated hydrocarbylthio or $-N(CH_3)OCH_3$, $R_a$ is a hydroxy-protecting group and $R_b$ is a carboxy-protecting group, and, as well as to the compound of formula I, to further new intermediates and methods for their preparation by Friedel-Crafts acylation.

3 Claims, No Drawings

OTHER PUBLICATIONS

P. Brower et al., Tetrahedron Letters, vol. 33, No. 17, pp. 2279-2282, (1992).
M.-P. Heck et al., J. Org. Chem., vol. 61, (1996), pp. 6486-6487.
Chem. Abstr. vol. 107, No. 19, abstract No. 175775m for J. Med. Chem. (1987), vol. 30 (10), pp. 1858-1878.
Chem. Abstr. vol. 121, No. 19, abstract No. 230347q for JP 06135975 (1994).
Beilstein Registry No. 6798562, Tetrahedron Lett., vol. 35, No. 13, (1994), pp. 1999-2002.
E. Santaniello et al., J. Org. Chem., vol. 53, (1988), pp. 1567-1569.
J. Monteiro et al., Synth. Commun., vol. 20, No. 3, (1990), pp. 315-319.
M. Scialdone et al., Tetrahedron Lett., vol. 36, No. 1, (1995), pp. 43-46.
G. Bertolini et al., Synth. Commun., vol. 24, (13), (1994), pp. 1833-1845.
Gopalan et al., Tetrahedron Letters, vol. 25, No. 46, (1984), pp. 5235-5238.
F. Kathawala et al., Helvetica Chimica Acta, vol. 69 (1986), pp. 803-805.
K. Takahashi et al., Bull. Chem. Soc. Jpn., vol. 68, (1995), pp. 2649-2656.
Santaniello, et al., J. Org. Chem. 1988, 53, 1567-1569.
R. Ohrlein, et al., Adv. Synth. Catal. 2003, 345, 713-715.

* cited by examiner

PROCESS FOR THE PREPARATION OF INTERMEDIATES USEFUL IN THE SYNTHESIS OF STATIN DERIVATIVES ESPECIALLY 7-AMINO-3,5-DIHYDROXYHEPANOIC ACID DERIVATIVES AND INTERMEDIATES THEREOF

This application is a divisional of application Ser. No. 10/482,463, filed on Dec. 31, 2003, now U.S. Pat. No. 7,420,074, which is a 371 of international app. No. PCT/EP2002/07307, filed Jul. 2, 2002, which claims priority to EP 018106708, filed Jul. 6, 2001, all of which are herein incorporated by reference.

SUMMARY OF THE INVENTION

The invention relates to novel preparation processes for the preparation of 3,5-dihydroxyheptanoic acid derivatives and to novel intermediates and processes for their preparation. The dihydroxyheptanoic acid derivatives and the intermediates are suitable for advantageous syntheses of statins.

BACKGROUND TO THE INVENTION

Statins are a class of pharmaceuticals that inhibit the enzyme hydroxymethylglutaryl CoA reductase (HMG-CoA-R) and are therefore widely used as hypolipidaemic agents and agents that lower the level of cholesterol in the blood (hypocholesterollipidaemic agents). All synthetically prepared HMG-CoA-R inhibitors have, as common structural features, an aromatic base structure and the so-called statin side chain, as symbolised by the following formula:

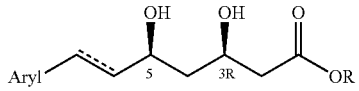

(wherein Aryl denotes aromatic, heterocyclic or aromatic-heterocyclic, unsubstituted or substituted, mono-, di- or polycyclic ring systems). Such a structural unit can be found in a whole range of pharmaceutically active agents, such as cerivastatin (Bayer AG), fluvastatin (Novartis), itavastatin (NK-104; Kowa Company Ltd.), BMY 22089 (Bristol-Myers Squibb), rosuvastatin (S-4522, AstraZeneca/Shionogi), glenvastin (Hoechst(Aventis) and atorvastatin (Warner-Lambert/Gödecke-Parke Davies/Pfizer).

The aim of the present invention is to provide new efficient methods of synthesising some known statin derivatives and to provide new intermediate compounds.

GENERAL DESCRIPTION OF THE INVENTION

Key steps in the synthesis according to the invention are early introduction of the correct absolute stereochemistry at C-3 (R) and subsequent regioselective chain lengthening. Unlike the linear synthesis processes in the prior art, the use of the novel statin side chain building blocks allows a convergent synthesis. The invention relates also to novel intermediates.

DETAILED DESCRIPTION OF THE INVENTION

The process according to the invention is based on the key intermediate of formula I

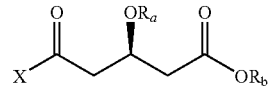

wherein X is halogen, acyloxy, activated hydrocarbyloxy, activated hydrocarbylthio or —N(CH$_3$)—OCH$_3$, R$_a$ is a hydroxy-protecting group and R$_b$ is a carboxy-protecting group, which intermediate is either ethenylated, as described below:

Starting from the reaction of the key intermediate of formula (I) with an ethylene of formula III

wherein Y$_a$ is halogen or hydrogen, there is obtained a keto compound of formula III

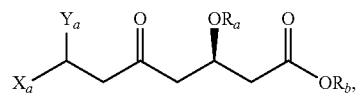

wherein Y$_a$ is halogen or hydrogen, X$_a$ is halogen (preferred) or acyloxy, R$_a$ is hydrogen (obtainable after selective removal of a hydroxy-protecting group R$_a$) or a hydroxy-protecting group and R$_b$ is a carboxy-protecting group; the compound of formula III is reacted further in one of the following three ways:

(1) A compound of formula III wherein Y$_a$ is hydrogen and X$_a$ is halogen (preferred) or acyloxy, while R$_a$ and R$_b$ are as defined for compounds of formula III, is reacted with a salt of hydrazoic acid to form an azido compound of formula IV

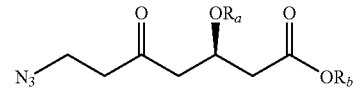

wherein R$_a$ is hydrogen or a hydroxy-protecting group and R$_b$ is a carboxy-protecting group. The compound of formula IV (when R$_a$ is a hydroxy-protecting group, after prior selective removal thereof) is then reduced diastereoselectively by means of a suitable reagent to form a syn-diol compound of formula V

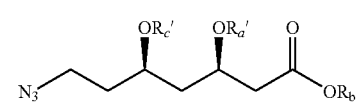

wherein R$_a$' is hydrogen and R$_c$' is hydrogen; or, after subsequent introduction of protecting groups, R$_a$' and R$_c$' are each independently of the other hydrogen or a protecting group, with the proviso that at least one of the two radicals is a protecting group, or $R_a'$ and $R_c'$ together are a bridging hydroxy-protecting group; and $R_b$ is a carboxy-protecting group;

and, in a case where the introduction of a bridging hydroxy-protecting group is desirable, when $R_a'$ and $R_c'$ are each hydrogen, the bridging hydroxy-protecting group formed by $R_a'$ and $R_c'$ together being introduced using a suitable reagent;

and the compound of formula V so obtainable is then reduced to the corresponding amino compound of formula VI

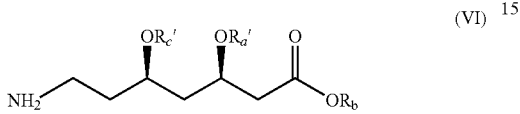

(VI)

wherein $R_a'$ and $R_c'$ are each independently of the other hydrogen or a hydroxy-protecting group or together are a bridging hydroxy-protecting group, and $R_b$ is a carboxy-protecting group.

That compound can then be used further directly for the preparation of a statin derivative the aryl radical of which is bonded to the side chain via nitrogen, for example for the preparation of atorvastatin analogously to the conditions described in WO 89/07598.

(2) Alternatively, a compound of formula III can be reacted as follows: a compound of formula III wherein $Y_a$ is hydrogen or halogen, iodine or especially chlorine or bromine and $X_a$ is halogen (preferred) or acyloxy, while $R_a$ and $R_b$ are as defined for compounds of formula III, is converted in the presence of a base, with elimination of hydrohalic acid HX, into an olefin of formula VII

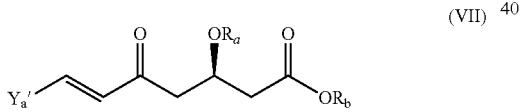

(VII)

wherein $Y_a'$ is hydrogen or halogen, especially iodine or more especially chlorine or bromine, $R_a$ is hydrogen or a hydroxy-protecting group and $R_b$ is a carboxy-protecting group. Such a compound is used further as described below under Variant (B), or the corresponding compound wherein $Y_a'$ is iodine can be obtained by reaction with an iodide salt.

The compound of formula VII, or the corresponding compound wherein $Y_a'$ is iodine, can then be converted into the corresponding HMG-CoA-reductase inhibitor, for example by Heck coupling with aryl iodides, aryl triflates or aryl bromides that introduce the complementary aryl radical for the formula described under "Background to the invention", or, after reduction of the double bond, can be used further.

Another further use of such a compound is brought about by reaction thereof with an iodide salt, the corresponding compound of formula VII wherein $Y_a'$ is iodine being obtained. The compound of formula VII, or the corresponding compound wherein $Y_a'$ is iodine, can then be converted into the corresponding HMG-CoA-reductase inhibitor, for example by Heck coupling with aryl iodides, aryl triflates or aryl bromides that introduce the complementary aryl radical for the formula described under "Background to the invention", or, after reduction of the double bond, can be used further.

For the preparation of other statins, preferably a compound of formula VII as obtained above wherein the radicals are as defined for formula VII, preferably wherein $Y_a'$=hydrogen, is then, if necessary, freed of a hydroxy-protecting group $R_a$ and subsequently reduced diastereoselectively by means of a suitable reagent to form a syn-diol compound of formula VIII

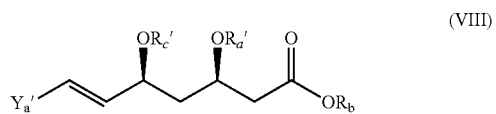

(VIII)

wherein $R_a'$ is hydrogen and $R_c'$ is hydrogen, or, after subsequent introduction of protecting groups, $R_a'$ and $R_c'$ are each independently of the other hydrogen or a protecting group, with the proviso that at least one of the two radicals is a protecting group, or $R_a'$ and $R_c'$ together are a bridging hydroxy-protecting group; $R_b$ is a carboxy-protecting group, and $Y_a'$ is hydrogen or halogen (especially iodine or more especially chlorine or bromine);

and, in a case where the introduction of a bridging hydroxy-protecting group is desirable, if necessary, when $R_a'$ and $R_c'$ are each hydrogen, the bridging hydroxy-protecting group formed by $R_a'$ and $R_c'$ together being introduced using a suitable reagent.

The resulting compound of formula VIII is then preferably cleaved oxidatively to form an aldehyde of formula IX

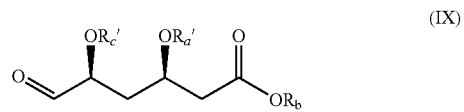

(IX)

wherein $R_a'$ and $R_c'$ are each independently of the other hydrogen or, preferably, a hydroxy-protecting group or together are a bridging hydroxy-protecting group; and $R_b'$ is a carboxy-protecting group; the compound of formula X can be used directly as synthon for the preparation of statin derivatives, especially of itavastatin (see Bull. Chem. Soc. Jpn. 68, 364 (1995)), BMY 22089 (see J. Med. Chem. 32, 2038 (1989)) or glenvastin (see Tetrahedron Lett. 31, 2545 (1990)), or it is reacted further with iodoform, diiodomethane or methyl iodide to form an iodine compound of formula X

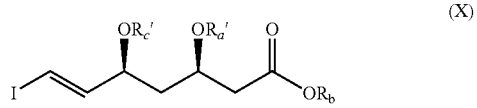

(X)

wherein $R_a'$, $R_b'$ and $R_c'$ are as defined for compounds of formula IX; if desired, one or more or all of the protecting groups can be removed therefrom. That compound can then be reacted under Suzuki coupling conditions, which may be modified if necessary, to form HMG-CoA-reductase inhibitors.

(3) As a third alternative (advantageous over reaction method
   (1), because the azide group is introduced only later and so the special precautionary measures to be taken when using azides are required only later), a compound of formula III wherein $X_a$ is halogen, especially iodine or more especially chlorine or bromine, or acyloxy, and $Y_a$ is hydrogen, (when $R_a$ is a hydroxy-protecting group, after removal thereof) $R_a$ is hydrogen and $R_b$ is a carboxy-protecting group can be converted diastereoselectively by means of a suitable reagent into a syn-diol compound of formula Va

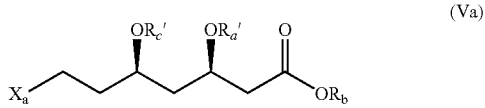
(Va)

wherein $X_a$ is halogen, especially iodine or more especially chlorine or bromine, or acyloxy, and $R_a'$ and $R_c'$ are as defined for compounds of formula V and $R_b$ is as defined for compounds of formula III; and the compound of formula Va is then reacted with a salt of hydrazoic acid to form a compound of formula V described above wherein $R_a'$ and $R_c'$ are each hydrogen or, after subsequent introduction of protecting groups, $R_a'$ and $R_c'$ are each independently of the other hydrogen or a protecting group, with the proviso that at least one of the two radicals is a protecting group, or $R_a'$ and $R_c'$ together are a bridging hydroxy-protecting group; and that compound is then reduced as described above under (1) to form an amino compound of formula VI, as defined above, which can then be used further as described above.

The invention relates also to a process for the preparation of the key intermediate of formula I as defined above.

For that purpose, a compound of formula XI

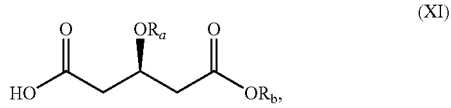
(XI)

wherein $R_a$ is a hydroxy-protecting group (or, less preferred because the ee is then lower, hydrogen) and $R_b$ is a carboxy-protecting group, is converted into the corresponding compound of formula I using a reagent that introduces the radical X.

The compound of formula XI is in turn advantageously prepared by hydrolysing a compound of formula XII

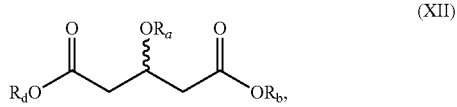
(XII)

wherein $R_a$ is a hydroxy-protecting group (or, less preferred because the ee is then lower, hydrogen), $R_b$ is a carboxy-protecting group and $R_d$ is hydrocarbyl, by means of an enantioselective catalyst (preferably by hydrolysis using a biocatalyst) with removal of the radical $R_d$, the corresponding compound of formula XI being obtained directly.

The compound of formula XII is advantageously obtained by reacting a glutaric acid derivative of formula XIII

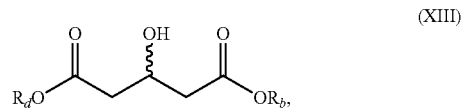
(XIII)

wherein $R_b$ and $R_d$ are as defined for compounds of formula XII, by introduction of a hydroxy-protecting group using the corresponding reagent suitable for the introduction of the protecting group. Examples of hydroxy protecting groups are given by T. W. Greene et al. in 'Protective Groups in Organic Chemistry', John Wiley, New York, $2^{nd}$ edition, 1991, p 88 ff.

The invention relates also to new individual steps of the processes described above, to new combinations of individual steps and to new intermediate compounds.

Unless indicated to the contrary, the general terms (including the reactions and reaction conditions) used hereinabove and hereinbelow preferably have the following meanings—these specific definitions and descriptions of reactions can be used independently of one another instead of the general terms mentioned hereinabove and hereinbelow, resulting in preferred embodiments of the invention:

The prefix "-lower" or "lower" indicates that the radical in question contains preferably up to 7 carbon atoms, especially up to 4 carbon atoms. Lower alkyl is therefore preferably $C_1$-$C_7$-alkyl, especially $C_1$-$C_4$alkyl, and may be unbranched or branched one or more times, insofar as possible. Unsaturated radicals, such as alkenyl or alkynyl, have at least two carbon atoms, preferably from 2 to 7, especially from 3 to 7, more especially 3 or 4.

In the processes mentioned hereinabove and hereinbelow, it is possible at any stage, even where not explicitly mentioned, for one or more or all of the protecting groups present in the compounds of formulae I to XIX in question to be removed or for one or more or all of the functional groups that are not to participate in the reaction, or that would interfere with the reaction, to be converted into protected groups by the introduction of suitable protecting groups (especially hydroxy-protecting groups and/or carboxy-protecting groups).

The protection of functional groups by such protecting groups, suitable reagents for their introduction, suitable protecting groups and reactions for their removal will be familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974.

Suitable hydroxy-protecting groups are especially selected from those of the acyl or ester type, e.g. lower alkanoyl, such as formyl, acetyl or isobutyroyl, benzoylformyl, chloroacetyl, dichloroacetyl, trichloroacetyl, trifluoroacetyl, methoxyacetyl, phenoxyacetyl, phenylacetyl, p-phenylacetyl, diphenylacetyl, 2,6-dichloro-4-methylphenoxyacetyl, 2,6- dichloro-4-(1,1,3,3-tetramethylbutyl)phenoxyacetyl, 2,4-bis (1,1-dimethylpropyl)phenoxyacetyl, chlorodiphenylacetyl, 3-phenylpropionyl, 4-azidobutyroyl, 4-methylthiomethoxybutyroyl, (E)-2-methyl-2-butenoyl, 4-nitro-4-methylpentanoyl, 4-pentenoyl, 4-oxopentanoyl, 4,4-(ethylenedithio) pentanoyl, 5-[3-bis(4-methoxyphenyl) hydroxymethylphenoxy)laevulinyl, pivaloyl, crotonoyl, monosuccinoyl, benzoyl, p-phenylbenzoyl, 2,4,6-trimethylbenzoyl, 2-(methylthiomethoxymethyl)benzoyl, 2-(chloroacetoxymethyl)benzoyl, 2-[(2-chloroacetoxy)ethyl]benzoyl, 2-[(2-benzyloxy)ethyl]benzoyl, 2-[2-(4-methoxybenzyloxy) ethyl]benzoyl, 2-iodobenzoyl, o-(dibromomethyl)benzoyl, o-(methoxycarbonyl)benzoyl, 2-chlorobenzoyl, 4-bromobenzoyl, 4-nitrobenzoyl, alkoxycarbonyl, such as methoxycarbonyl, ethoxycarbonyl, isobutoxycarbonyl, methoxymethylcarbonyl, 9-fluorenylmethoxycarbonyl, 2,2,2-trichloroethoxycarbonyl, 1,1-dimethyl-2,2,2-trichloroethoxycarbonyl, 2-(trimethylsilyl)ethoxycarbonyl, 2-(phenylsulfonyl)ethoxycarbonyl, 2-(triphenylphosphonio) ethoxycarbonyl, vinyloxycarbonyl, allyloxycarbonyl, p-nitrophenoxycarbonyl, benzyloxycarbonyl, p-methoxybenzyloxycarbonyl, 3,4-dimethoxybenzyloxycarbonyl, o-nitrobenzyloxycarbonyl, p-nitrobenzyloxycarbonyl, dansylethoxycarbonyl, 2-(4-nitrophenyl)ethoxycarbonyl, 2-(2, 4-dinitrophenyl)ethoxycarbonyl, 2-cyano-1-phenylethoxycarbonyl, S-benzylthiocarbonyl, 4-ethoxy-1-naphthyloxycarbonyl, 3',5'-dimethoxybenzoinyloxycarbonyl, 2-methylthiomethoxyethoxycarbonyl, N-phenylcarbamoyl, dimethylethylphosphinothiolyl, methyldithiocarbonyl; N,N, N',N'-tetramethylphosphorodiamidoyl, sulfonyl, methanesulfonyl, benzenesulfonyl, toluenesulfonyl, 2-[(4-nitrophenyl)ethyl]sulfonyl, allylsulfonyl, 2-formylbenzenesulfonyl, nitroxy, or protecting groups of the ether type, such as methyl, substituted methyl, preferably lower alkoxymethyl, especially methoxymethyl (MOM), methylthiomethyl, (phenyldimethylsilyl)methoxymethyl, benzyloxymethyl, p-methoxybenzyloxymethyl, p-nitrobenzyloxymethyl, guaiacolmethyl, tert-butoxymethyl, 4-pentenyloxymethyl, silyloxymethyl, lower alkoxy-lower alkoxymethyl, especially 2-methoxyethoxymethyl (MEM), 2,2,2-trichloroethoxymethyl, 2-(trimethylsilyl)-ethoxymethyl or menthoxymethyl, tetrahydropyranyl, 3-bromotetrahydropyranyl, tetrahydrothiopyranyl, 4-methoxytetrahydropyranyl, 1-methoxycyclohexyl, 4-methoxytetrahydrothiopyranyl, S,S-dioxy-4-methoxytetrahydrothiopyranyl, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl; substituted ethyl, such as 1-ethoxyethyl, 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2, 2-trichloroethyl, 1,1,1,3,3,3-hexafluoro-2-phenylisopropyl, 2-trimethylsilylethyl, 2-(benzylthio)ethyl, 2-(phenylselenyl) ethyl, tert-butyl; allyl or propargyl, substituted phenyl ethers, such as p-chlorophenyl, p-methoxyphenyl, p-nitrophenyl, 2,4-dinitrophenyl or 2,3,5,6-tetrafluoro-4-(trifluoromethyl) phenyl, benzyl, substituted benzyl, such as p-methoxybenzyl, 3,4-dimethoxybenzyl, o-nitrobenzyl, p-nitrobenzyl, p-halobenzyl, e.g. p-bromobenzyl, 2,6-dichlorobenzyl, p-cyanobenzyl, p-phenylbenzyl, 2,6-difluorobenzyl, p-azidobenzyl, 4-azido-3-chlorobenzyl, 2-trifluoromethylbenzyl or p-(methylsulfinyl)benzyl, 2- or 4-picolyl, 3-methyl-2-picolyl, 2-quinolinylmethyl, 1-pyrenylmethyl, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl), 4,4',4"-tris(laevulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrahydrobenzo[a,c,g,i]fluorenylmethyl)-4',4"-dimethoxytrityl, 9-anthryl, 9-(9-phenyl)xanthenyl, 9-(9-phenyl-10-oxo)anthryl, 1,3-benzodithiolan-2-yl, S,S-dioxo-benzoisothiazolyl; of the silyl ether type, such as tri-lower alkylsilyl, e.g. trimethylsilyl, triethylsilyl, triisopropylsilyl, dimethylisopropylsilyl, diethylisopropylsilyl, dimethylthexylsilyl, tert-butyldimethylsilyl or di-tert-butylmethylsilyl, tert-butyldiphenylsilyl, triphenylsilyl, diphenylmethylsilyl, tris(trimethylsilyl)silyl, (2-hydroxystyryl)dimethylsilyl, (2-hydroxystyryl)diisopropylsilyl, tert-butylmethoxyphenylsilyl or tert-butoxydiphenylsilyl.

Bridging protecting groups can likewise be used where a molecule contains two hydroxy groups (for example bridging hydroxy-protecting groups formed by $R_a$ and $R_c$ or $R_a'$ and $R_c'$ together) or a hydroxy-protecting group and a carboxy group (for example bridging protecting groups formed by $R_a$ and $R_b$ or $R_a'$ and $R_b$ in the molecules of the corresponding formulae mentioned hereinabove and hereinbelow in which those radicals are present).

A bridging hydroxy-protecting group (especially one formed by $R_a'$ and $R_c'$) is preferably selected from methylene, ethylidene, tert-butylmethylidene, 1-tert-butylethylidene, 1-phenylethylidene, 1-(4-methoxyphenyl)ethylidene, 2,2,2-trichloroethylidene, vinylmethylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene, 4-nitrobenzylidene, mesitylene, phenyl-(1,2-bis(methylenyl)), methoxymethylene, ethoxymethylene, dialkylsilylene, such as tert-butylsilylene, 1,3-(1,1,3,3-tetraisopropyldisiloxanylidene), 1,1,3,3-tetra-tert-butoxydisiloxanylidene, —C(=O)—, ethylboronyl (—(H$_3$C—CH$_2$)B—), phenylboronyl (-(phenyl)B—), o-acetamidophenylboronyl or especially isopropylidene.

Carboxy-protecting groups are especially ester-forming, enzymatically and/or chemically removable protecting groups, preferably enzymatically and/or chemically removable protecting groups, such as heptyl, 2-N-(morpholino) ethyl, cholinyl, methoxyethoxyethyl or methoxyethyl; or those which are primarily chemically removable, e.g. alkyl, such as lower alkyl, especially methyl, ethyl, substituted lower alkyl (except for benzyl and substituted benzyl), such as substituted methyl, especially 9-fluorenylmethyl, methoxymethyl, methoxyethoxymethyl, methylthiomethyl, 2-(trimethylsilyl)ethoxym ethyl, benzyloxymethyl, pivaloyloxymethyl, phenylacetoxymethyl, triisopropylsilylmethyl, 1,3-dithianyl-2-methyl, dicyclopropylmethyl, acetonyl, phenacyl, p-bromophenacyl, α-methylphenacyl, p-methoxyphenacyl, desyl, carbamidomethyl, p-azobenzenecarboxamidomethyl, N-phthalimidomethyl or 4-picolyl, 2-substituted ethyl, especially 2-iodo-, 2-bromo- or 2-chloro-ethyl, 2,2,2-trichloroethyl, 2-(trimethylsilyl)ethyl, 2-methylthioethyl, 2-(p-nitrophenylsulfenyl)ethyl, 2-(p-toluenesulfonyl) ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl or 2-cyanoethyl, tert-butyl, 3-methyl-3-pentyl, 2,4-dimethyl-3-pentyl or ω-chloro-lower alkyl, especially 4-chlorobutyl or 5-chloropentyl, cyclopentyl, cyclohexyl, lower alkenyl, especially allyl, methallyl, 2-methylbut-3-en-2-yl, 3-methylbut-2-enyl or 3-buten-1-yl, substituted lower alkenyl, especially 4-(trimethylsilyl)-2-buten-1-yl, cinnamyl or α-methylcinnamyl, lower alkynyl, such as prop-2-ynyl, phenyl, substituted phenyl, especially 2,6-dialkylphenyl, such as 2,6-dimethylphenyl, 2,6-diisopropylphenyl, 2,6-di-tert-butyl-4-methylphenyl, 2,6-di-tert-butyl-4-methoxyphenyl, p-(methylthio)phenyl or pentafluorophenyl, benzyl, substituted benzyl, especially triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxocyclohexylidene)-3-methylbutyl]amino}benzyl, piperonyl or p-polymer-benzyl, tetrahydropyranyl, tetrahydrofuranyl, or silyl radicals, such as tri-lower alkylsilyl, especially trimethylsilyl, triethylsilyl, tert-butyldimethylsilyl, isopropyldimethylsilyl or di-tert-butylmethylsilyl, or phenyl-di-lower alkylsilyl, such as phenyldimethylsilyl; alternatively a carboxy group can also be protected in the form an oxazolyl, 2-alkyl-1,3-oxazolinyl, 4-alkyl-5-oxo-1,3-oxazolidinyl or 2,2-bistrifluoromethyl-4-alkyl-5-oxo-1,3-oxazolidinyl radical.

Amide-protecting groups are especially allyl, tert-butyl, N-methoxy, N-benzoyloxy, N-methylthio, triphenylmethylthio, tert-butyldimethylsilyl, triisopropylsilyl, 4-(methoxymethoxy)phenyl, 2-methoxy-1-naphthyl, 9-fluorenyl, tert-butoxycarbonyl, N-benzyloxycarbonyl, N-methoxy- or N-ethoxy-carbonyl, toluenesulfonyl, N-buten-1-yl, 2-methoxycarbonylvinyl, or especially alkyl, such as lower alkyl, or more especially substituted alkyl, especially benzyl, benzyl substituted by one or more radicals selected from lower alkoxy, such as methoxy, lower alkanoyloxy, such as acetoxy, lower alkylsulfinyl, such as methylsulfinyl, dicyclopropylmethyl, methoxymethyl, methylthiomethyl and N-benzoyloxymethyl; or bis(trimethylsilyl)methyl, trichloroethoxymethyl, tert-butyldimethylsilyloxymethyl, pivaloyloxymethyl, cyanomethyl, benzyl, 4-methoxybenzyl, 2,4-dimethoxybenzyl, 3,4-dimethoxybenzyl, 2-acetoxy-4-methoxybenzyl, o-nitrobenzyl, bis(4-methoxyphenyl)phenylmethyl, bis(4-methylsulfinylphenyl)methyl, pyrrolidinomethyl, diethoxymethyl, 1-methoxy-2,2-dimethylpropyl or 2-(4-methylsulfonyl)ethyl.

It is characteristic of protecting groups that they are simple to remove (that is to say without undesirable secondary reactions taking place), for example by solvolysis, reduction, photolysis or alternatively under conditions analogous to physiological conditions, for example enzymatically.

The person skilled in the art will know which protecting groups can be used for which reactions and compounds of formulae I to XIX. In the case of compounds of formula I that are to be converted into compounds of formula III, it is advisable to use especially those protecting groups which would not also react during the (Friedel-Crafts-analogous) reaction, that is to say without aryl radicals, such as phenyl radicals. Hydroxy-protecting groups $R_a$ and $R_a'$ are especially those which can be selectively introduced and removed, more especially those which are not removed during the conversion of compounds of formula XII. Here it is especially advisable to use hydroxy-protecting groups that do not contain too strongly electronegative substituents, more especially lower alkanoyl, such as acetyl, lower alkoxy-lower alkanoyl, such as methoxyacetyl, or protecting groups of the substituted methyl type, especially lower alkylmethyl, more especially methoxymethyl (MOM), or lower alkoxy-lower alkoxymethyl, especially 2-methoxyethoxymethyl (MEM).

Acyloxy in formula I or III is especially the radical of an organic carboxylic or sulfonic acid having from 1 to 24 carbon atoms, unsubstituted or substituted by one or more radicals, especially from 1 to 3 radicals, preferably selected from lower alkoxy, halogen, nitro, lower alkoxycarbonyl, phenyl, phenyl-lower alkyl, phenyloxy, lower alkanoyloxy, benzoyloxy, di-lower alkyl-amino, N-phenyl-lower alkyl-N-lower alkyl-amino, N,N-di(phenyl-lower alkyl)amino, carbamoyl, thiocarbamoyl, sulfamoyl and cyano, and saturated or partially or fully unsaturated, and is preferably the radical of an alkanecarboxylic acid or haloalkanecarboxylic acid, especially lower alkanoyl, of an arylcarboxylic acid, especially benzoic acid, or halo-lower alkanesulfonyl, such as trifluoromethanesulfonyl; or, in the case of a compound of formula I, a radical of formula I'

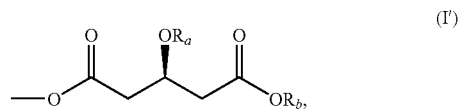

wherein $R_a$ and $R_b$ are as defined for compounds of formula I (the compound of formula I is then a symmetric anhydride (obtainable, for example, by reaction of the acid of formula I (OH instead of X) in the presence of a lower alkanecarboxylic acid anhydride, such as acetic anhydride, in the presence of catalytic amounts of acid)).

Activated hydrocarbyloxy or hydrocarbylthio is preferably unsubstituted or substituted lower alkyloxy, unsubstituted or substituted aryloxy (preferably having from 6 to 12 ring atoms) or unsubstituted or substituted heterocyclyloxy (preferably an unsaturated, fully or partially saturated mono- or bi-cyclic ring system having from 4 to 12 ring atoms and up to three hetero atoms selected from nitrogen, sulfur and oxygen) and is especially lower alkyloxy substituted in the 1-position by esterified carbonyl, such as lower alkoxycarbonyl, cyano or by phenylcarbonyl, especially lower alkoxycarbonylmethoxy, such as ethoxycarbonylmethoxy, cyanomethoxy or phenacyloxy (Ph-CO—CH$_2$—O—), tert-butylthio, N-benzotriazolyloxy, N-succinimidyloxy, pyridyloxy or pyridylthio, especially 2-pyridyloxy or more especially 2-pyridylthio, or electronegatively substituted aryloxy, such as p-nitrophenyloxy, 2,4-dinitrophenyloxy, pentafluorophenyloxy or 2,4,5-trichlorophenyloxy.

The reaction of the key intermediate of formula (I) with an ethylene of formula II is effected preferably in the presence of a Lewis acid, such as FeCl$_3$, SbCl$_5$, SnCl$_4$, BF$_3$, TiCl$_4$, ZnCl$_2$ or especially aluminium chloride (AlCl$_3$), preferably in a suitable solvent, especially a halogenated hydrocarbon, such as chloroform, methylene chloride or ethylene chloride, at preferred temperatures of from −10° C. to the reflux temperature, especially from 0 to 30° C.

Any hydroxy-protecting groups $R_a$ can then, if necessary, be removed selectively from the compound of formula III by customary methods, especially by the methods described in the standard works mentioned above.

"Selectively" means especially enzymatically. In particular, lower alkanoyl, such as acetyl, is removed enzymatically, for example by esterases, such as pig's liver esterase, in suitable buffers, such as phosphate buffer, at preferred pH values of from 5 to 9, especially from 6 to 8. Further possible enzymes and reaction conditions will be found below under the definition of biocatalysts for the hydrolysis. Lower alkoxymethyl, such as MOM, or lower alkoxy-lower alkoxymethyl, such as MEM, is removed by chemical standard methods.

The reaction of a compound of formula III wherein $Y_a$ is hydrogen and $X_a$ is halogen, while $R_a$ and $R_b$ are as defined for compounds of formula III, with a salt of hydrazoic acid to form a compound of formula IV, as defined above, or of a compound of formula Va wherein $X_a$ is halogen, especially iodine or especially chlorine or bromine, while $R_a$ and $R_b$ are as defined for compounds of formula II, with a salt of hydrazoic acid to form a compound of formula V, as defined above, is preferably carried out with such a salt in the presence of a complex-forming agent for the metal cation, especially with an alkali metal azide, such as sodium or potassium azide, in the presence of a crown ether, especially 18-crown-6-ether, in a suitable solvent, preferably an aprotic solvent, such as a di-lower alkyl-lower alkanoylamide, e.g. dimethylformamide or dimethylacetamide, or a di-lower alkyl sulfoxide, e.g dimethyl sulfoxide, or the like. The reaction can alternatively be carried out under conditions of phase transfer catalysis, i.e. in the presence of two-phase systems, such as water/organic solvent (such as halogenated hydrocarbons, e.g. methylene chloride, chloroform or dichloroethane), in the presence of lipophilic quaternary ammonium salts, such as hydrogen sulfate or chloride, e.g. tetrabutylammonium hydrogen sulfate, Aliquat 336, Adogen 464 (both consisting primarily of methyltrioctylammonium chloride), preferably tetra-lower alkylammonium bromide or iodide, such as tetrabutylammonium bromide or iodide or the like, the base being present in the aqueous phase.

The diastereoselective reduction of the obtainable azido compound of formula IV (if necessary after removal of the hydroxy-protecting group $R_a$, preferably as described above for the removal of the hydroxy-protecting group $R_a$ from a compound of formula III) to form a compound of formula V; of a compound of formula III (if necessary after removal of the hydroxy-protecting group $R_a$ (from a compound of formula II) as described above) to form a compound of formula V; in each case as defined above and below, is then preferably carried out in a chelate-controlled manner, there being used as chelate-forming agent preferably a di-lower alkyl borinic acid lower alkyl ester, especially diethyl borinic acid ethyl ester. The reduction of the chelated β-hydroxyketone of formula III is then effected with a complex hydride, preferably with an alkali metal borohydride, especially with sodium borohydride. As solvent there are preferably used ethers, such as cyclic ethers, especially tetrahydrofuran, and/or alcohols, such as lower alkanols, e.g. methanol, the preferred reaction temperatures being from –80 to –30° C., especially from –78 to –40° C.

In addition, preferred is the diastereoselective reduction of compound of formula III, wherein $X_a$ is halogen, especially chlorine or bromine or more especially chlorine, and $Y_a$ is hydrogen, $R_a$ is hydrogen and $R_b$ is a carboxy-protecting group; is reacted with hydrogen in the presence of an alkali metal salt or alkaline-earth metal salt and a heterogeneous platinum catalyst to form a syn-diol compound of formula Va

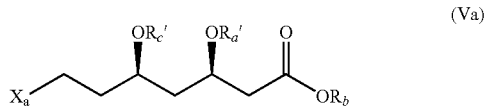

(Va)

wherein $X_a$ is halogen, especially chlorine or bromine or more especially chlorine, and $R_a'$ and $R_c'$ are as defined for compounds of formula V and $R_b$ is a carboxy-protecting group. Preferred salt is an alkaline-earth metal salt, most preferred is a magnesium salt, and especially preferred is magnesium acetate. Customary, this diastereoselctive reduction is carried under pressure between 1 to 100 bar at temperatures between 0 to 100° C. Most preferably the reduction is carried out using platinum on carbon catalyts together with magnesium acetate with hydrogen under a pressure of 6 to 60 bar at temperatures between 10 to 60° C.

In a broader embodiment of the invention it is also preferred to use alternative reducing agents, such as sodium cyanoborohydride, but this results in lower diastereoselectivity and is therefore less preferred.

When it is desirable or necessary subsequently to introduce a protecting group into the compound of formula V or Va ($R_a'$, $R_c'$ or $R_a'$ and $R_c'$ as protecting group, especially $R_a'$ and $R_c'$ together as a bridging protecting group), this is carried out under standard conditions, preferably as described in the above-mentioned standard works.

The bridging protecting group formed by $R_a'$ and $R_c'$ together, preferably as indicated above, especially the isopropylidene protecting group, is especially introduced by standard methods, preferably as described in the standard works mentioned above, in the case of the isopropylidene protecting group especially by reaction with acetone or, preferably, with a di-lower alkoxypropane, such as dimethoxypropane, in the presence of copper(II) sulfate, zinc chloride or, preferably, an acid, such as sulfuric acid or especially an organic sulfonic acid, such as an arylsulfonic acid (wherein aryl has especially from 6 to 10 ring atoms, e.g. naphthyl or phenyl, and is unsubstituted or mono- or poly-substituted, especially up to tri-substituted, especially by lower alkyl, such as methyl), preferably toluenesulfonic acid, or with a lower alkyl isopropenyl ether, such as ethyl isopropenyl ether, in the presence of an arylsulfonic acid. As preferred solvents there are used aprotic solvents, such as ethers, especially cyclic ethers, more especially tetrahydrofuran, or carboxylic acid amides, such as di-lower alkyl-lower alkanoylamides, e.g. dimethylformamide. The preferred reaction temperatures are in the range of from 0 to 80° C., especially from 20 to 30° C.

The reduction of the azide of formula V to the amine of formula VI is preferably carried out with a complex hydride, or with tributyltin; or preferably by catalytic hydrogenation, for example with hydrogen and platinium or palladium on activated carbon, preferably in an alcohol, such as methanol or ethanol, at hydrogen pressures of from 0.5 to 20 bar, for example at 10 bar, at temperatures of from 0 to 50° C., especially from 15 to 35° C. Alternatively, the reduction can be effected by reaction with a tertiary phosphine and subsequent treatment with water (Staudinger reduction).

The reaction of a compound of formula III wherein $Y_a$ is hydrogen or halogen, especially iodine or more especially chlorine or bromine, and $X_a$ is halogen, while $R_a$ and $R_b$ are as defined for compounds of formula II, in the presence of a base, with elimination of hydrohalic acid HX, to form an olefin of formula VII is preferably carried out in the presence of a base selected from a nitrogen base, especially a tertiary amine, such as a tri-lower alkylamine, e.g. triethylamine, pyridine, quinoline, di-lower alkylaniline, such as dimethylaniline, dicyclohexylethylamine, amidines, such as 1,5-diazabicyclo[4.3.0]non-5-ene or 1,8-diazabicyclo[5.4.0]undec-7-ene, or a different base selected from alkali metal hydroxides, metal carbonates or hydrogen carbonates, alkali metal alcoholates in the corresponding alcohol or inert solvents, such as dimethyl sulfoxide, e.g. potassium tert-butyl alcoholate, alkali metal amides in inert solvents or the like. Where a solvent is used, preferred solvents are ethers, such as diethyl ether, di-lower alkyl-lower alkanoylamides, such as dimethyl- or diethylformamide or -acetamide, or the solvents already mentioned. The preferred reaction temperatures are from −20° C. to the reflux temperature of the reaction mixture in question, preferably from −10 to 30° C.

The reaction with an iodide salt to form the corresponding compound of formula VII wherein $Y_a'$ is iodine is then preferably effected with a metal iodide, especially an alkali metal iodide, such as sodium iodide, in the presence of a Lewis acid, especially aluminium chloride, in a suitable solvent, preferably a ketone, such as acetone, at preferred temperatures in the range of from 0 to 50° C., especially from 20 to 30° C.

The reduction of a compound of formula VII, if necessary after removal of the hydroxy-protecting group $R_a$ by methods described in the standard works, preferably as described for the removal of hydroxy-protecting groups $R_a$ from the compound of formula II, is then effected diastereoselectively, under conditions analogous to those described for the diastereoselective reduction of compounds of formula IV, to form the corresponding syn-diol compound of formula VIII.

If necessary, the protecting groups $R_a'$ and/or $R_c'$ or a bridging protecting group formed by $R_a'$ and $R_c'$ are introduced into that compound under conditions analogous to those described for the introduction of protecting groups in a compound of formula V.

The oxidative cleavage of a compound of formula VIII to form an aldehyde of formula IX is then carried out preferably by ozonolysis and subsequent working-up of the primary product with a suitable reducing agent, especially triphenylphosphine, dimethylsulfide or zinc/acetic acid, there being used as solvent preferably a halogenated hydrocarbon, especially methylene chloride, and the preferred temperatures for the reaction with ozone being from −80 to −50° C., preferably from −78 to 60° C., and for the subsequent working-up from −20 to 50° C., preferably from 20 to 30° C.; or by reaction with Os(VIII), preferably $OsO_4$ (used as such, in catalytic amounts in the presence of stoichiometric amounts of N-methylmorphine-N-oxide (NMO) or peroxides, such as hydrogen peroxide, or prepared in situ, for example by oxidation of catalytic amounts of $K_2OsO_4$ with stoichiometric amounts of NMO) or with permanganates, preferably potassium permanganate, the reaction with Os(VIII) or permanganates preferably being effected in a polar solvent, such as an alcohol, e.g. ethanol, and/or water, if desired in the presence of inert salts, such as magnesium sulfate, at preferred temperatures of from −20 to 40° C., for example from −10 to 20° C.; the oxidative cleavage of the intermediate diol (not described) is then carried out with an alkali metal periodate, especially $NaIO_4$ (in a water-containing medium), or with $H_5IO_6$ (in a water-containing or anhydrous medium), or less preferably with lead tetraacetate (in an anhydrous medium).

The reaction of an aldehyde of formula IX with iodoform ($CHI_3$), diiodomethane or methyl iodide to form an iodine compound of formula X is carried out especially in the presence of a chromium(II) halide, especially chromium dichloride, under protective gas in a suitable solvent, such as an ether, especially tetrahydrofuran, at preferred temperatures of from −10 to 50° C., especially from −5 to 30° C.

The reaction for the preparation of a compound of formula XI to form the corresponding compound of formula I is preferably effected under customary conditions, there being used as reagent for introducing a radical X especially an acid anhydride or an acid halide, preferably an inorganic acid halide, more especially a phosphorus trihalide, phosphorus pentahalide or thionyl halide, such as phosphoryl chloride, phosphoryl bromide, phosphorus trichloride, phosphorus tribromide, phosphorus pentachloride, phosphorus pentabromide, thionyl chloride or thionyl bromide, a symmetric anhydride of a lower alkanesulfonic acid halogenated at the α-carbon atom, such as trifluoromethanesulfonic anhydride, or an acid chloride or a symmetric anhydride of an organic carboxylic acid, especially an oxalyl halide, such as oxalyl chloride or bromide, the reaction being carried out in the absence or preferably presence of a (preferably polar) solvent or solvent mixture, especially in a halogenated hydrocarbon, preferably methylene chloride, in the absence or presence of an acid amide, especially a di-lower alkyl-lower alkanoic acid amide, such as dimethylformamide, at preferred temperatures of from −20° C. to the reflux temperature of the reaction mixture in question, preferably from −10 to 50° C.

Preference is given to lower alkyl, especially methyl or more especially ethyl, or lower alkoxy-lower alkyl, especially methoxymethyl.

The preparation of a compound of formula XI is preferably effected with removal of the hydrocarbyl radical $R_d$ in the presence of an enantioselective catalyst, especially a biocatalyst.

As biocatalysts for the hydrolysis there are suitable cells or ruptured cells with the enzymes mentioned below, or especially enzymes as such, preferably esterases, lipases and proteases (peptidases or amidases, see U. T. Bornscheuer and R. T. Kazlauskas, in: Hydrolases in Organic Synthesis, Wiley-VCH, 1999, pages 65-195, ISBN 3-527-30104-6). Common representatives of those classes of enzyme are especially animal esterases (e.g. pig's liver esterase=PLE, pig's pancreas esterase=PPL), esterases from microorganisms or fungi (*B. subtilis* esterase, *Pichia* esterases, yeast esterases, *Rhizopus* sp. esterases (RML, ROL), *Penicillium* sp. esterases, *G. candidum* (GCL), *H. lanuginosa* (HLL), *Candida* sp. (CAL-A, CAL-B, CCL), *Aspergillus* sp. (ANL), *Pseudomonas* sp. (PCL, PFL) and the like), and also proteases, e.g. subtilisin, thermitase, chymotrypsin, thermolysin, papain, aminoacylases, penicillin amidases, trypsin or the like, to name only a few. The person skilled in the art will be familiar with further suitable enzymes, and the enzymes that can be used are not limited to those mentioned in the above list. Such enzymes can be obtained in the form of crude isolates and/or in purified form from natural sources and/or from recombinant microorganisms by means of modern cloning procedures via overexpression, amplification or the like. Commercially available enzymes are especially preferred. The enzymes can be present as such or immobilised or adsorbed on carriers, for example on silica gel, kieselguhr, such as Celite®, Eupergit® (Röhm & Haas, Darmstadt, Germany) or the like, or used in the form of "CLECs" (cross-linked enzymes), such as are available from ALTUS BIOLOGICS, the scope for use extending beyond the list given, as the person skilled in the art will know (see U. T. Bornscheuer and R. T. Kazlauskas, in: Hydrolases in Organic Synthesis, Wiley-VCH, 1999, pages 61-64, ISBN 3-527-30104-6; K. Faber in: Biotransformation in Organic Chemistry, Springer 1997, Third Edition, pages 345-357, ISBN 3-540-61688-8; H. J. Rehm, G. Reed in: Biotechnology, VCH 1998, Second Edition, pages 407-411). The enzymes can be used in pure organic solvents, e.g. liquid hydrocarbons, such as hexane, toluene or benzene, liquid ethers, such as diethyl ether, methyl tert-butyl ether or tetrahydrofuran, liquid halogenated hydrocarbons, such as methylene chloride, water or aqueous buffer solutions, in mixtures of those solvents, for example mixtures of one or more thereof with water or aqueous buffer solutions. The aqueous solution is preferably buffered, pH 5-9, it being possible to use customary buffer systems (see e.g. K. Faber in: Biotransformation in Organic Chemistry, Springer 1997, Third Edition, p. 305; or U. T. Bornscheuer and R. T. Kazlauskas, in: Hydrolases in Organic Synthesis, Wiley-VCH, 1999, pages 61-65). The pH is preferably kept substantially constant during the reaction. Most suitable for this purpose is an automatic titrator having a standardised acid or base solution, or manual titration. The reaction temperature is preferably in the range from 10 to 50° C., especially from 25 to 40° C. The amount of biocatalyst used and the concentrations of the reagents can be dependent upon the substrate and the reaction conditions (temperature, solvent etc.) selected in each case, as will be known to the person skilled in the art. There are preferably used commercially available enzymes (for example from Fluka, Sigma, Novo Nordisk, Amano, Roche and the like) or those listed in the current literature (see e.g. H.-J. Rehm, G. Reed in: Biotechnology, VCH 1998, $2^{nd}$ Edition, pages 40-42). Especially preferred for the preparation of enantiomerically pure compounds is α-chymotrypsin in phosphate buffer, especially at pH 7.0.

Unless otherwise indicated, halogen is preferably fluorine, chorine, bromine or iodine.

Wherever solvents are mentioned hereinabove and hereinbelow it is also possible, where expedient and possible, for mixtures of two or more of the mentioned solvents to be used.

The person skilled in the art will know that for certain reactions such solvents or solvent mixtures must be used in anhydrous (absolute) form and that, if necessary, also the reaction vessels used must have dry surfaces.

Where necessary, the said reactions are carried out in the absence of oxygen, and often also in the absence of carbon dioxide and/or atmospheric moisture, for example under protective gas, such as argon or nitrogen.

Where possible, the starting compounds and intermediate compounds can also be used in the form of salts, obtained in the form of salts or converted into salts in accordance with customary processes, for example in the case of carboxy compounds into the corresponding metal salts, such as alkali metal salts, e.g. sodium or potassium salts, or alkaline earth metal salts, such as calcium salts, or salts with nitrogen bases, such as ammonium, tri-lower alkylammonium, pyridinium salts or the like. Where salt formation is possible, any reference to any of the compounds should be understood as also including the corresponding salts.

In addition to the solvents already mentioned, it is also possible to use other suitable solvents, where expedient and possible for the reaction in question. Such solvents can be selected, for example, from the following list: water, esters, e.g. lower alkyl-lower alkanoates, such as diethyl acetate, ethers, e.g. aliphatic ethers, such as diethyl ether, or cyclic ethers, such as dioxane or tetrahydrofuran, liquid aromatic hydrocarbons, such as benzene or toluene, alcohols, such as methanol, ethanol or 1- or 2-propanol, nitrites, such as acetonitrile, halogenated hydrocarbons, such as dichloromethane, chloroform or ethylene chloride, acid amides, such as dimethylformamide, bases, e.g. heterocyclic nitrogen bases, such as pyridine, carboxylic acids, such as lower alkanecarboxylic acids, e.g. acetic acid, carboxylic acid anhydrides, e.g. lower alkanoic acid anhydrides, e.g. acetic anhydride, cyclic, linear or branched hydrocarbons, such as cyclohexane, hexane or isopentane, or mixtures of such solvents or other solvents, e.g. aqueous solutions. Such solvents and solvent mixtures can also be used in working-up, e.g. by chromatography or partition. Any mention of solvents or eluants hereinabove and hereinbelow should be understood as including also mixtures of such solvents or eluants.

The other compounds, especially of formula II, are known, can be prepared according to methods known per se and/or are commercially available.

PREFERRED EMBODIMENTS OF THE INVENTION

Preferred aspects of the invention can be found in the claims which are incorporated herein by reference.

Hereinabove and hereinbelow, the radicals in compounds of formulae I to XIX have the meanings given hereinabove and hereinbelow (especially the specific meanings mentioned for certain reaction variants or methods), and the reaction conditions are in each case as defined hereinabove or hereinbelow, preferably as the preferred reaction conditions:

Preference is given to a process for the preparation of statin derivatives which comprises the preparation of a compound of formula I, as defined hereinabove and hereinbelow, from a compound of formula XI, preferably such a process for the preparation of a compound of formula I; the compound of formula XI in turn preferably being prepared from a compound of formula XII which, in turn, is preferably prepared from a compound of formula XIII.

Also preferred is a process for the preparation of statin derivatives, especially of statin precursors of formulae VI, IX and/or X, which comprises the reaction of a key intermediate of formula I. Compound of formula I reacts with an ethylene of formula II to form a keto compound of formula III, which is reacted in accordance with one of methods (1), (2) and (3), method (1) comprising reaction to form an azido compound of formula IV, which is then converted into a syn-diol compound of formula V and then into an amino compound of formula VI; or according to method (2) is converted into an olefin of formula VII; or according to method (3) is converted into a compound of formula Va, which is then converted into an azide of formula V, which is then converted into an amino compound of formula VI; and preferably the compound of formula VII obtained according to method (2), unless used directly for the preparation of statin derivatives (if desired after conversion into the corresponding compound wherein $Y_a'$ is iodine), is reduced to form a syn-diol compound of formula VIII, which in turn is then cleaved oxidatively to form an aldehyde of formula IX, which, if desired, is then converted into an iodine compound of formula X.

Also preferred is a process for the preparation of statin derivatives, especially of compounds of formula VI, which comprises the reaction of a compound of formula I with an ethylene of formula II to form a compound of formula II, conversion thereof into an azide of formula IV, reduction to a compound of formula V and conversion thereof into an amino compound VI; or especially conversion thereof into a syn-diol of formula Va, subsequent conversion thereof into a compound of formula V and conversion thereof into an amino compound VI.

Preference is given also to a process for the preparation of statin derivatives, especially of statin precursors of formula VII, preferably of formula VIII, especially of formula IX, more especially of formula X, which comprises the reaction of the key intermediate of formula I with an ethylene of formula II to form a keto compound of formula III and reaction thereof to form a compound of formula VII; which is preferably reduced diastereoselectively for the preparation of a compound of formula VIII, which is especially cleaved oxidatively for the preparation of a compound of formula IX, which is especially converted into an iodine compound of formula X.

Also preferred is a process for the preparation of statin derivatives, especially of statin precursors of formula VII, preferably of formula VIII, especially of formula IX, more especially of formula X, which comprises the reaction of the key intermediate of formula I with a compound of formula III to form a compound of formula VII; which is preferably reduced diastereoselectively for the preparation of a compound of formula VIII, which is especially cleaved oxidatively for the preparation of a compound of formula IX, which is especially converted into an iodine compound of formula X.

In all the preferred embodiments, if necessary one or more or all of the protecting groups present are removed or one or more or all of the functional groups that are not to participate in a reaction, or that would interfere with the reaction, are converted into protected groups by the introduction of suitable protecting groups (especially hydroxy-protecting groups and/or carboxy-protecting groups); and, where salt-forming groups are present and the reaction in question is not impaired, the compounds of formulae I to XIX may also be in salt form.

Of the compounds, the invention relates especially to those of formulae I, III, IV, V, VII and VIII as such, especially those in which the substituents correspond to the radicals indicated in the respective Examples.

Special preference is given to the compounds 1d, 1e, 2a, 2b, 2c, 2d, 2e, 2f, 3a, 3b, 3d, 3e, 4a, 4b, 6a, 6b, 6c, 6d, 6e, 6f, and Bb mentioned in the Examples, especially each individual compound.

The present invention relates especially to the reaction steps and new intermediate compounds mentioned in the following Examples.

EXAMPLES

The following Examples serve to illustrate the invention but do not limit the scope thereof.

Abbreviations Used:
Celite Celite®, filtration aid based on kieselguhr, trade mark of Celite Corp., USA
TLC thin-layer chromatography
DMF dimethylformamide
eq. equivalent
h hour(s)
Hünig's base N-ethyldiisopropylamine min minute(s)
NMR nuclear magnetic resonance spectroscopy
PLE pig's liver esterase
m.p. melting point (° C.)
THF tetrahydrofuran
torr unit of pressure (mm mercury column); 1 torr corresponds to 0.1333 kPa Unless otherwise indicated, the ratios of the components of eluant mixtures, solvent mixtures and the like are given in parts by volume (v/v).

Reaction scheme I for Examples 1 to 4:

[Structure A: RO-C(O)-CH₂-CH(OH)-CH₂-C(O)-OR]
→
[Structure B: RO-C(O)-CH₂-CH(OA)-CH₂-C(O)-OR]

↓ ee 98-99%

[Structure C: HO-C(O)-CH₂-CH(OA)-CH₂-C(O)-OR]

a: A = C(O)CH₃
b: A = C(O)CH₂OCH₃
c: A = CH₂OCH₃
d: A = CH₂OCH₂CH₂OCH₃

R = CH₂CH₃

[Structure D: Phenylethyl-NH-C(O)-CH₂-CH(OH)-CH₂-C(O)-OR]

Example 1 a) Precursor of formula Ba wherein R=ethyl, A=acetyl (diethyl-3-acetoxyglutaric acid)

54.0 g of diethyl-3-hydroxyglutaric acid (Fluka, Buchs, Switzerland) are dissolved at room temperature in 26.5 ml of pyridine and 27.4 ml of acetic anhydride and the mixture is stirred for about 12 h until all the starting material has reacted. The mixture is diluted with ethyl acetate and washed in succession with water, 1N hydrochloric acid, saturated sodium hydrogen carbonate solution and saturated sodium chloride solution. The organic phase is separated and dried over magnesium sulfate. After evaporation of the organic solvent, 64.3 g of NMR-spectroscopically pure acetate, the title compound, remain: $^1$H-NMR (CDCl$_3$): 1.24 (t, 6H); 2.01 (s, 3H); 2.69 (d, 4H); 4.14 (q, 4H); 5.50 (quin., 1H).

b) Compound of formula Ca wherein R=ethyl, A=acetyl (monoethyl-3(R)-acetoxyglutaric acid)

160 g of diethyl-3-acetoxyglutaric acid Ba are suspended at room temperature in 570 ml of distilled water, and 168 ml of 0.1M phosphate buffer (pH 7) are added. After the addition of 2.7 g of α-chymotrypsin (Sigma, Sigma Chemie, Buchs, Switzerland), the mixture is stirred vigorously and maintained at pH 7.8 using a pH meter and pH stat (Metrohm) and 0.5N sodium hydroxide solution. When the theoretical amount of hydroxide solution (1.3 liters) has been consumed, the mixture is extracted with ethyl acetate. The aqueous phase is adjusted to pH 1 with concentrated hydrochloric acid (conc. HCl) and then extracted with ethyl acetate. Any cloudiness of the organic phase can be removed by filtration over Celite. After evaporation of the organic phase, 131 g (97%) of semi-ester Ca remain: $^1$H-NMR (CDCl$_3$): 1.25 (t, 3H); 2.03 (s, 3H); 2.71 (d, 2H); 2.77 (d, 2H); 4.14 (q, 2H); 5.50 (quin., 1H).

c) Determination of the Enantiomeric Excess (ee) of the Monoacid Ca by Means of the Amide Da (R=ethyl, A=acetyl)

150 mg of the monoacid Ca are reacted in accordance with the customary methods of peptide coupling with 341 mg of (benzotriazol-1-yloxy)-tris(dimethylamino)phosphonium hexafluorophosphate, 246 mg of Hünig's base and 931 μl of R-phenylethylamine (Fluka, Buchs, Switzerland) in 1.5 ml of DMF at room temperature. After customary extraction, 188 mg of amide Da are obtained. NMR spectroscopy indicates a diastereoisomeric ratio of 99:1 on the basis of the shift difference between the two diastereoisomeric acetates and accordingly a ratio of R to S of 99:1. HPLC analysis (column: Chiracel OJ 25 cm×0.46 cm (Daicel Chemical Industries, Ltd., JP), n-hexane:ethanol=95:5, flow rate 1.2 ml/min, UV detection at 210 nm) confirms the ratio of R to S as 98.8:1.2. $^1$H-NMR (CDCl$_3$): 1.15 (t, 3H); 1.35 (d, 3H); 1.85 and 1.87 (2×s, total 3H, ratio as 99:1); 2.47 (m, 2H); 2.55 (dd, 1H); 2.65 (d, 1H); 4.01 (broad q, 1H); 5.00 (quint., 1H); 5.38 (m, 1H); 6.51 (broad d, NH); 7.20 (m, 5H).

Example 2 a) Precursor of formula Bb Wherein R=ethyl, A=methoxyacetyl
(diethyl-3-methoxyacetoxyglutaric acid)

50.0 g of diethyl-3-hydroxyglutaric acid (Fluka, Buchs, Switzerland) are dissolved at 0° C. in 80 ml of dichloromethane; 20.6 ml of pyridine and 22.9 ml of methoxyacetyl chloride are added and the mixture is stirred at room temperature for about 12 h until all the starting material has reacted. The mixture is washed in succession with water, 1N hydrochloric acid, saturated sodium hydrogen carbonate solution and saturated sodium chloride solution. The organic phase is separated and dried over magnesium sulfate. After evaporation of the organic solvent, a dark-yellow syrup is obtained which is filtered over a small amount of silica gel using hexane/ethyl acetate (2:1). After evaporation of the solvent, 65.0 g of NMR-spectroscopically pure methoxyacetate Bb are obtained: $^1$H-NMR (CDCl$_3$): 1.20 (t, 3H); 2.65 (d, 4H); 3.35 (s, 3H); 3.90 (s, 2H); 4.04 (q, 4H); 5.55 (quin., 1H).

b) Compound of formula Cb wherein R=ethyl, A=methoxyacetyl
(monoethyl-3(R)methoxyacetoxyglutaric acid)

40.0 g of diethyl-3-methoxyacetoxyglutaric acid Bb are suspended at room temperature in 150 ml of distilled water, and 43 ml of 0.1M phosphate buffer (pH 7) are added. After the addition of 0.4 g of α-chymotrypsin (Sigma; Sigma Chemie, Buchs, Switzerland), the mixture is stirred vigorously and maintained at pH 7.8 using a pH meter and pH stat (Metrohm) and 0.5N sodium hydroxide solution. After 18 h, a further 0.1 g of chymotrypsin is added and stirring is continued until the theoretical amount of hydroxide solution has been consumed. The mixture is then extracted with ethyl acetate (4×). The aqueous phase is adjusted to pH 1 with concentrated hydrochloric acid (conc. HCl) and then extracted with ethyl acetate. Any cloudiness of the organic phase can be removed by filtration over Celite. After evaporation of the organic phase, 24.8 g of semi-ester Cb remain: $^1$H-NMR (CDCl$_3$): 1.24 (t, 3H); 2.74 (d, 2H); 2.75 (d, 2H); 3.42 (s, 3H); 3.99 (s, 2H); 4.14 (q, 2H); 5.59 (quin., 1H).

Alternatively, immobilised chymotrypsin can also advantageously be used. It can be supported on silica gel (Sigma S0507, 230-400 mesh, average pore diameter 0.6 nm; Sigma Chemie, Buchs, Switzerland) by customary methods without loss of activity, easily removed and then used repeatedly.

c) Determination of the Enantiomeric Excess (ee) of the Monoacid Cb by Means of Benzamide Db
(R=Ethyl, A=Methoxyacetyl)

200 mg of the monoacid Cb are reacted by customary methods of peptide coupling with 392 mg of (benzotriazol-1-yloxy)-tris(dimethylamino)phosphonium hexafluorophosphate, 290 µl of Hünig's base and 88 µl of benzylamine (Fluka, Buchs, Switzerland) in 2.0 ml of DMF at room temperature. After customary extraction, 178 mg of amide Db are obtained. HPLC analysis (Chiracel OD 25 cm×0.46 cm (Daicel Chemical Industries, Ltd., JP), n-hexane:ethanol=9:1, flow rate 1 ml/min, UV detection at 210 nm) yields a ratio of R to S of 98.6:1.4. $^1$H-NMR (CDCl$_3$): 1.22 (t, I=7.0, 3H); 2.62 (d, I=6.5, 2H); 2.75 (dd, I=15.8, 5.3, 2H); 3.35 (s, 3H); 3.91 (s, 2H); 4.10 (q, I=7.0, 2H); 4.38 (d, I=5.9, 2H); 5.56-5.65 (m, 1H); 6.31 (t, br, NH); 7.21-7.33 (m, 5H).

d) Purification of the compound Cb wherein R=ethyl, A=methoxyacetyl
(monoethyl-3(R)methoxyacetoxyglutaric acid)

500 g of monoacid Cb are dissolved in 2 liters of tert-butyl methyl ether and heated to boiling. 400 ml (1 eq.) of dicyclohexylamine dissolved in 2 liters of tert-butyl methyl ether are added dropwise in the course of 10 min, followed by 4 liters of n-hexane. If crystallisation does not start spontaneously, seeding is carried out, followed by cooling to 5-10° C. The resulting crystals are filtered off with suction and dried in vacuo at 70° C. Yield: 694 g, 80% white crystals, m.p.=111° C. 3 g of the resulting salt are dissolved in 20 ml of water, NaCl is added to the solution and 1 eq. of 3N hydrochloric acid is added. The precipitated dicyclohexylamine hydrochloride is filtered off with suction and the clear filtrate is extracted repeatedly with tert-butyl methyl ether. After drying and removal of the solvent, 1.6 g, 92%, of monoacid Cb are obtained; ee≧99.5%, determined by way of the benzamide analogously to c).

Example 3 a) Precursor of formula Bc wherein R=ethyl, A=methoxymethyl
(diethyl-3-methoxymethoxyglutaric acid)

97.2 g of diethyl-3-hydroxyglutaric acid A (Fluka) are dissolved at 0° C. together with 210 ml of formaldehyde dimethylacetal in 350 ml of dichloromethane, and 61.3 g of phosphorus pentoxide are added in portions. The mixture is stirred vigorously overnight, the temperature of the mixture rising to room temperature. When conversion is complete (TLC monitoring), the mixture is decanted off, diluted with methylene chloride and washed in succession with 2×saturated sodium hydrogen carbonate solution and saturated sodium chloride solution. The organic phase is separated and dried over magnesium sulfate. After evaporation of the solvent, a colourless fluid is obtained which is distilled at 98-101° C./0.17 torr. 104.8 g (89%) of a colourless fluid, the title compound, are obtained: $^1$H-NMR (CDCl$_3$): 1.15 (t, 3H); 2.53 (m, 4H); 3.24 (s, 3H); 4.05 (q, 4H); 4.30 (quin., 1H); 4.58 (s, 2H).

b) Compound of formula Cc wherein R=ethyl, A=methoxymethyl
(monoethyl-3(R)methoxymethoxyglutaric acid)

980 mg of diethyl-3-methoxymethoxyglutaric acid Bc are suspended at room temperature in 16 ml of distilled water, and 16 ml of 0.1M phosphate buffer (pH 7) are added. After the addition of 0.5 g of chymotrypsin, the mixture is stirred vigorously and maintained at pH 7.8 using a pH meter and pH stat (Metrohm) and 0.5N sodium hydrogen carbonate solution. When the theoretical amount of carbonate solution has been consumed, the mixture is extracted with ethyl acetate. The aqueous phase is adjusted to pH 3-3.5 with 0.5N hydrochloric acid and then extracted with ethyl acetate. Any cloudiness of the organic phase can be removed by filtration over Celite. After washing of the organic phase with saturated sodium chloride solution and evaporation of the organic phase, 0.67 g (77%) of spectroscopically clean monoacid, the title compound, remain: $^1$H-NMR (CDCl$_3$): 1.24 (t, 3H); 2.69 (m, 4H); 3.34 (s, 3H); 4.13 (q, 2H); 4.38 (quin., 1H); 4.68 (s, 2H).

c) Determination of the Enantiomeric Excess (ee) of the Monoacid Cc by Means of the Amide with Benzylamine 400 mg of the monoacid are reacted by customary methods for peptide coupling with 760 mg of (benzotriazolyl-1-yloxy)-tris(dimethylamino)phosphonium hexafluorophosphate, 215 μl of Hünig's base and 0.70 ml of benzylamine (Fluka) in 2.0 ml of DMF at from 0° C. to room temperature. After customary extraction, 567 mg of amide are obtained. HPLC analysis (Chiralcel OD, 25×0.46 cm, n-hexane:ethanol=98:2, 1 ml/min) confirms a ratio of R to S of more than 98:2. $^1$H-NMR (CDCl$_3$): 1.19 (t, 3H), 2.48 (dd, 2H); 2.56 (dd, 1H); 3.24 (s, 2H); 4.06 (broad q, 1H); 4.34 (m, 3H); 4.59 (m, 2H); 7.00 (broad s, NH); 7.20 (m, 5H).

Example 4 a) Precursor of formula Bd wherein R=ethyl, A=2-methoxyethoxymethyl (diethyl-3-(2-methoxyethyl)-oxymethoxyglutaric acid)

At 0° C., 11.23 g of diethyl-3-hydroxyglutaric acid A (Fluka) are introduced together with 11.8 ml of diisopropylethylamine into 40 ml of dichloromethane, and 8.6 g of 2-methoxyethoxymethyl chloride (Fluka) are added. The mixture is stirred vigorously overnight, the temperature of the mixture rising to room temperature. The mixture is diluted with methylene chloride and washed in succession with 2×1N hydrochloric acid, 2×saturated sodium hydrogen carbonate solution and saturated sodium chloride solution. The organic phase is separated and dried over magnesium sulfate. After evaporation of the solvent, a colourless liquid is obtained, 15.9 g (99%), the title compound. $^1$H-NMR (CDCl$_3$): 1.20 (t, 3H); 2.59 (m, 4H); 3.32 (s, 3H); 3.49 (m, 2H); 3.63 (m, 2H); 4.09 (q, 4H); 4.36 (quin, 1H); 4.73 (s, 2H).

b) Compound of formula Cd wherein R=ethyl, A=2-methoxyethyl (monoethyl-3(R)-(2-methoxyethyl)-oxymethoxyglutaric acid)

2 g of diethyl-3-(2-methoxyethyl)-oxymethoxyglutaric acid Bd are suspended at room temperature in 30 ml of distilled water, and 3.3 ml of 0.1M phosphate buffer (pH 7) are added. After the addition of 0.1 g of chymotrypsin, the mixture is stirred vigorously and maintained at pH 7.8 using a pH meter and pH stat (Metrohm) and 0.5N sodium hydroxide solution. When the theoretical amount of hydroxide solution has been consumed, the mixture is extracted with ethyl acetate. The aqueous phase is adjusted to pH 3-3.5 with 0.5N hydrochloric acid and then extracted with ethyl acetate. Any cloudiness of the organic phase can be removed by filtration over Celite. After washing of the organic phase with saturated sodium chloride solution and evaporation of the organic phase, 1.44 g (79%) of spectroscopically clean monoacid, the title compound, remain: $^1$H-NMR (CDCl$_3$): 1.25 (t, 3H); 2.02 (s, 3H); 2.67 (m, 4H); 3.38 (s, 3H); 3.55 (m, 2H); 3.69 (m, 2H); 4.12 (q, 4H); 4.41 (quin., 1H); 4.79 (q, 2H).

c) Determination of the enantiomeric excess (ee) of the monoacid Cc by means of the amide Dc ((R=ethyl, Ac=2-methoxyethoxymethyl)

380 mg of the monoacid Cd are reacted in accordance with customary methods for peptide coupling with 682 mg of (benzotriazolyl-1-yloxy)-tris(dimethylamino)phosphonium hexafluorophosphate, 493 μl of Hünig's base and 185 μl of R-phenylethylamine (Fluka) in 3.0 ml of DMF at from 0° C. to room temperature. After customary extraction, 403 mg of amide are obtained. NMR-spectroscopy indicates a diastereoisomeric ratio of greater than 95:5 on the basis of the shift difference between the two methoxy groups in the diastereoisomers. HPLC analysis (Chiralcel OD, 25×0.46 cm, n-hexane:ethanol=95:5, 1 ml/min) confirms the ratio of R to S as 98:2. $^1$H-NMR (CDCl$_3$): 1.22 (t, 3H), 1.45 (d, 3H); 2.48 (m, 2H); 2.62 (m, 2H); 3.30 (s, ca. 5%); 3.38 (s, 95%); 3.50 (m, 4H); 4.12 (1, 1H); 4.34 (quint., 1H); 4.79 (q, 2H); 5.11 (quint., 1H); 6.54 (broad d, NH), 7.34 (m, 5H).

Reaction scheme II for Examples 5, 6 and 7 (the radicals being as defined in the Examples):

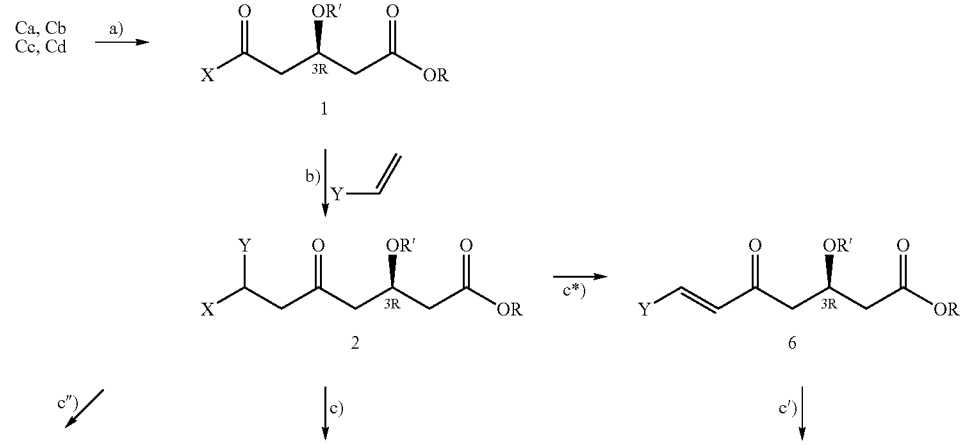

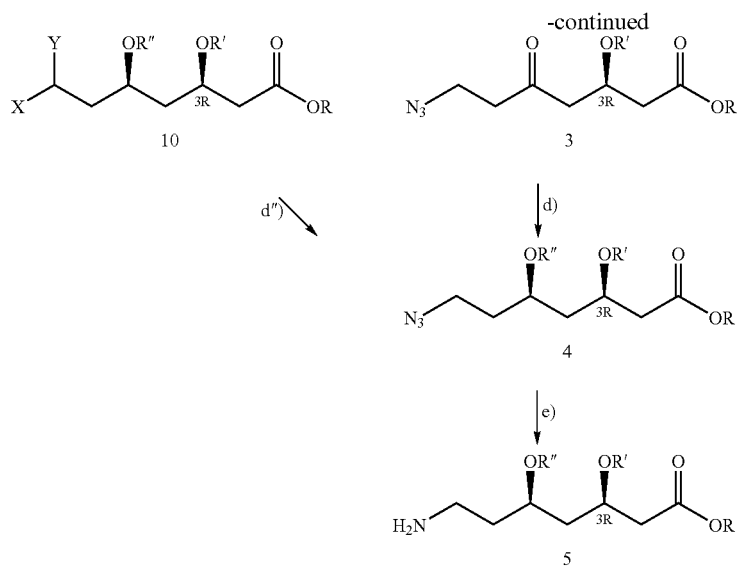

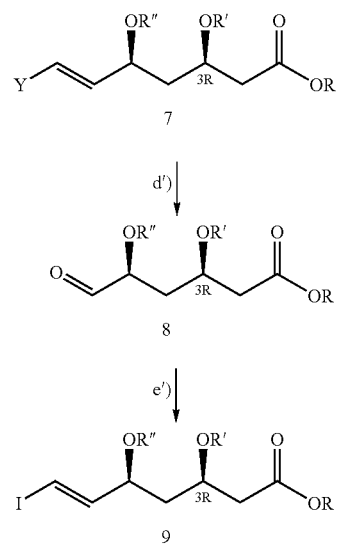

Example 5

Glutaric Acid Semihalides of Formula 1 a) Monoethyl ester of (3R)-acetoxy-glutaric acid chloride 1a (R=ethyl, X=Cl, R'=acetyl)

30.0 g of (3R)-acetoxyglutaric acid monoethyl ester (Ca) are dissolved in 60 ml of dry dichloromethane to which 20 drops of dry DMF have been added, and at 0-5° C. the solution is slowly treated with 21.9 g of oxalyl chloride. The mixture is then stirred for about 30 min. at 0° C. and then for a further 1.5 h at room temperature until the evolution of gas can no longer be observed. After evaporation of the solvent, 32.6 g of NMR-spectroscopically pure acid chloride 1a remain. (Colourless product can be obtained after molecular distillation). $^1$H-NMR (CDCl$_3$): 1.25 (t, 3H); 2.04 (s, 3H); 2.66 (dd, 1H); 2.70 (dd, 1H); 3.30 (dd, 1H); 3.34 (dd, 1H); 4.16 (q, 2H); 5.47 (m, 1H).

b) Monoethyl ester of (3R)-acetoxyglutaric acid bromide 1b (R=ethyl, X=Br, R'=acetyl)

5.0 g of (3R)-acetoxyglutaric acid monoethyl ester (Ca) are dissolved in 18 ml of dry dichloromethane to which a drop of dry DMF has been added, and at 0-5° C. the solution is slowly treated with 6.7 g of oxalyl bromide. The mixture is then stirred for about 30 min. at 0° C. and then for a further 2 h at room temperature until the evolution of gas can no longer be observed. After evaporation of the solvent, 6.6 g (98%) of spectroscopically pure acid bromide 1b remain: $^1$H-NMR (CDCl$_3$): 1.21 (t, 3H); 2.00 (s, 3H); 2.62 (dd, 1H); 3.39 (dd, 1H); 3.42 (dd, 1H); 4.11 (q, 2H); 5.41 (m, 1H).

c) Monoethyl ester of (3R)-methoxyacetoxyglutaric acid chloride 1c (R=ethyl, X=Cl, R'=methoxyacetyl)

21.0 g of monoethyl-3(R)-methoxyacetoxyglutaric acid Cb are dissolved in 100 ml of dry dichloromethane to which 40 μl of dry DMF has been added, and at 0-5° C. the solution is slowly treated with 13.9 g of oxalyl chloride. The mixture is then stirred for about 4 h, the temperature of the mixture rising to room temperature. The mixture is then diluted with ethyl acetate and extracted 3× with ice-water, and the organic phase is dried over sodium sulfate. After evaporation of the solvent, 20.9 g of NMR-spectroscopically pure acid chloride 1c remain: $^1$H-NMR (CDCl$_3$): 1.20 (t, 3H); 2.04 (s, 3H); 2.67 (m, 2H); 3.32 (m, 2H); 3.36 (s, 3H); 3.95 (s, 2H); 4.09 (q, 2H); 5.52 (m, 1H).

d) Monoethyl ester of (3R)-methoxymethoxyglutaric acid chloride 1d (R=ethyl, X=Cl, R'=methoxymethyl)

0.40 g of the monoacid Cc is dissolved in 2 ml of dry dichloromethane to which 3 drops of dry DMF are added, and at 0-5° C. the solution is slowly treated with 0.18 ml of oxalyl chloride until the evolution of gas can no longer be observed. After evaporation of the solvent, 0.43 g of acid chloride 1d remains: $^1$H-NMR (CDCl$_3$): 1.25 (t, 3H); 2.67 (m, 4H); 3.69 (s, 3H); 4.13 (q, 2H); 5.53 (q, 1H); 5.54 (s, 2H).

e) Monoethyl ester of (3R)-(2-methoxyethyl)-oxymethoxyglutaric acid chloride 1e (R=ethyl, X=Cl, R'=2-methoxyethyloxymethyl)

0.53 g of the monoacid Cd is dissolved in 2 ml of dry dichloromethane to which 2 drops of dry DMF have been added, and at 0-5° C. the solution is slowly treated with 0.21 ml of oxalyl chloride until the evolution of gas can no longer be observed. After evaporation of the solvent, 0.54 g of acid chloride 1e remains: $^1$H-NMR (CDCl$_3$): 1.21 (t, 3H); 2.55 (m, 1H); 2.65 (m, 1H); 3.24 (m, 2H); 3.34 (s, 3H); 3.50 (m, 2H); 3.65 (m, 2H); 4.10 (q, 2H); 4.38 (quint., 1H); 4.74 (m, 2H).

Example 6

Preparation of the Compounds 5 and the Associated Intermediates 2, 3 and 4 and of Compounds 6; and Also of Compounds 7, 8, 9 and 10

(i) (b) 3(R)-Acetoxy-7-chloro-5-oxo-heptanoic acid ethyl ester 2a (R=ethyl, R'=acetyl, X=Cl, Y=H): 10.0 g of acid chloride 1a are dissolved at room temperature in 25 ml of dry ethylene chloride and added dropwise in the course of 15 min to 16.5 g of aluminium trichloride in 50 ml of ethylene chloride, a slight rise in temperature being observed. Dry ethylene gas is passed through the resulting suspension, the temperature rising to about 40° C. and the suspension being largely dissolved. When the absorption of gas has ceased, the mixture is poured into ice-cold saturated sodium chloride solution, and the organic phase is separated and washed a further 2× with saturated sodium chloride solution. The resulting oil is decolorised in ether over activated carbon. 11.1 g of chloride 2a are obtained: $^1$H-NMR (CDCl$_3$): 1.17 (t, 3H); 1.93 (s, 3H); 2.59 (m, 2H); 2.79 (m, 2H); 2.85 (dt, 2H); 3.65 (t, 2H); 4.04 (broad q, 2H); 5.43 (m, 1H).

(ii) (Conversion according to (b)) 3(R)-7-Chloro-3-hydroxy-5-oxo-heptanoic acid ethyl ester 2b (R=ethyl, R'=H, X=Cl, Y=H): 0.40 g of the acetylated chlorine compound 2a is dissolved in 2 ml of ethanol and 10 ml of potassium dihydrogen phosphate buffer (0.05M, pH 7), and 0.01 g of esterase (PLE) (Boehringer Mannheim) is added. The pH is maintained at a constant value using pH stat and 0.5M sodium hydroxide solution and the reaction is extracted with ethyl acetate when the theoretical amount of base has been consumed. After removal of the solvent, the residue is purified by chromatography on silica gel. 0.30 g of deacetylated chlorine compound 2b is obtained: $^1$H-NMR (CDCl$_3$): 1.22 (t, 3H); 2.49 (m, 2H); 2.65 (m, 2H); 2.91 (m, 2H); 3.70 (t, 2H); 4.13 (q, 2H); 4.46 (m, 1H).

(iii) (b) 3(R)-Acetoxy-7,7-dichloro-5-oxo-heptanoic acid ethyl ester 2c (R=ethyl, R'=acetyl, X=Cl, Y=Cl): 10.0 g of acid chloride 1a are dissolved in 12 ml of dry ethylene chloride and at 0° C. added dropwise in the course of 15 min to 110 ml of ethylene chloride. 18.6 g of aluminium chloride are added to the resulting solution, a slight increase in temperature being recorded. Vinyl chloride is passed through the initially clear solution, with vigorous stirring. After about 30 min, a suspension is obtained. When the absorption of gas has ceased, about 90 min, the mixture is poured into ice-cold saturated sodium chloride solution and then extracted with methylene chloride. The organic phase is separated off and washed in succession twice with saturated sodium chloride solution and saturated sodium hydrogen carbonate solution. After drying over sodium sulfate, a deep-brown oil is obtained which is filtered over Celite and activated carbon using ethyl acetate. In order to separate polymeric material, fractional filtration is carried out over a short column of silica gel. 11.5 g of chloride 2c are obtained: $^1$H-NMR (CDCl$_3$): 1.24 (t, 3H); 2.00 (s, 3H); 2.65 (d, 2H); 2.86 (d, 2H); 3.38 (d, 2H); 4.11 (q, 2H); 5.48 (m, 1H); 6.08 (t, 1H).

(iv) (b) 3(R)-Methoxymethoxy-7-chloro-5-oxo-heptanoic acid ethyl ester 2d (R=ethyl, R'=methoxymethyl, X=Cl, Y=H): The compound is prepared under conditions analogous to those described for Example 6 (i), starting from 1d.

(v) (b) 3(R)-(2-Methoxyethyl)-oxymethoxy-7-chloro-5-oxo-heptanoic acid ethyl ester 2e (R=ethyl, R'=2-methoxyethyl-oxymethyl, X=Cl, Y=H): The compound is prepared under conditions analogous to those described for Example 6 (i), starting from 1e.

(vi) (c*) 3(R)-Acetoxy-7-chloro-5-oxo-hept-6-enoic acid ethyl ester 6a (R=ethyl, R'=acetyl, Y=Cl): 11.4 g of chloroketone 2c are dissolved at 0° C. in 100 ml of dry diethyl ether, and 5.28 ml of triethylamine are added. When the reaction has ceased (about 4 h), the mixture is extracted in succession with saturated sodium chloride solution, 1N hydrochloric acid (2×), sodium hydrogen carbonate solution and saturated sodium chloride solution. The organic phase is dried over magnesium sulfate and evaporated off. 7.1 g (71%) of α,β-unsaturated ketone 6a are obtained in the form of a dark-red oil. The material is pure enough for further reactions. The ketone can be chromatographed on silica gel. 6a: $^1$H-NMR (CDCl$_3$): 1.20 (t, 3H); 1.96 (s, 3H); 2.63 (m, 2H); 2.90 (m, 2H); 4.08 (q, 2H); 5.46 (m, 1H); 6.49 (d, 1H, 15.0 Hz); 7.32 (d, 1H, 15.0 Hz).

(vii) (Conversion according to (c*)) 3(R)-Acetoxy-7-iodo-5-oxo-hept-6-enoic acid ethyl ester 6b (R=ethyl, R'=acetyl, Y=I): The chlorine compound 6a, 7.1 g, is dissolved at room temperature in 50 ml of dry acetone, and 8.1 g of sodium iodide are added. A clear red solution is formed, to which 0.36 g of aluminium chloride is added. A precipitate is formed momentarily. The mixture is stirred for about a further 6 h, then diluted with ether and extracted in succession with saturated sodium chloride solution and water. After drying over sodium sulfate and removal of the solvent, 9.4 g of the iodine compound 6b are obtained, which is further used immediately. It can, however, also be further purified by chromatography over silica gel. 6b: $^1$H-NMR (CDCl$_3$): 1.22 (t, 3H); 1.96 (s, 3H); 2.64 (m, 2H); 2.90 (m, 2H); 4.10 (q, 2H); 5.47 (m, 1H); 7.12 (d, 1H, 15.0 Hz); 7.88 (d, 1H, 15.0 Hz).

(viii) (c*) 3(R)-Acetoxy-5-oxohept-6-enoic acid ethyl ester 6c (R=ethyl, R'=acetyl, Y=H): 1.0 g of chloroketone 2a is dissolved at room temperature in 10 ml of dry diethyl ether, and 0.55 ml of triethylamine is added. When the reaction is complete, the mixture is poured into ice-cold 1N hydrochloric acid, and the organic phase is separated and extracted in succession with saturated sodium hydrogen carbonate solution and saturated sodium chloride solution. The organic phase is dried over magnesium sulfate and evaporated. 0.62 g (71%) of α,β-unsaturated ketone 6c is obtained after chromatographic purification over silica gel: $^1$H-NMR (CDCl$_3$): 1.17 (t, 3H); 1.92 (s, 3H); 2.60 (m, 2H); 2.92 (m, 2H); 4.06 (broad q, 2H); 5.43 (m, 1H); 5.84 (dd, 1H); 6.21 (m, 2H).

(ix) (c*) 3(R)-Methoxymethoxy-5-oxohept-6-enoic acid ethyl ester 6d (R=ethyl, R'=methoxymethyl, Y=H): The compound is prepared starting from 2d analogously to Example 6 (viii).

(x) (c*) 3(R)-(2-Methoxyethyl)-oxymethoxy-5-oxohept-6-enoic acid ethyl ester 6e (R=ethyl, R'=2-methoxyethyl-oxymethyl, Y=H): The compound is prepared starting from 2e analogously to Example 6 (viii).

(xi) (c) 3(R)-Acetoxy-7-azido-5-oxo-heptanoic acid ethyl ester 3a (R=ethyl, R'=acetyl): 2.5 g of chloroketone 2a are dissolved in 5 ml of dimethylformamide, and 0.68 g of sodium azide and 0.03 g of 18-crown-6-ether are added. The mixture is stirred at room temperature until the reaction is complete, then diluted with ethyl acetate and extracted in succession with water and saturated sodium chloride solution. After evaporation of the solvent, 2.1 g of azide 3a are obtained: $^1$H-NMR (CDCl$_3$): 1.23 (t, 3H); 1.98 (s, 3H); 2.63 (dd, 2H); 2.68 (ddd, 2H); 2.83 (dd, 2H); 3.52 (t, 2H); 4.10 (q, 2H); 5.49 (m, 1H). $[\alpha_D]=-23.4°$ (c=1, CHCl$_3$).

(xii) (Conversion according to (c)) 3(R)-7-Azido-3-hydroxy-5-oxo-heptanoic acid ethyl ester 3b (R=ethyl, R'=H): 0.47 g of azido compound 3a is dissolved in 10 ml of phosphate buffer (0.05M, pH 7) which contains 2.0 ml of ethanol, and 0.01 g of Chirazyme E1 (PLE, Roche) is added. Using a pH stat and a titrator (0.5M NaOH), the pH is maintained at 7 and the reaction is extracted with ethyl acetate when the theoretical amount of sodium hydroxide solution has been consumed. The organic phase is then extracted by shaking with saturated sodium chloride solution and dried over magnesium sulfate. After removal of the solvent and subsequent column chromatography over silica gel, 0.34 g of deacylated product 3b is obtained: $^1$H-NMR (CFCl$_3$): 1.32 (t, 3H); 2.57 (m, 2H); 2.79 (m, 4H); 2.83 (dd, 2H); 3.61 (t, 2H); 4.22 (q, 2H); 4.54 (m, 1H).

(xiii) (c) 3(R)-Methoxymethoxy-7-azido-5-oxo-heptanoic acid ethyl ester 3d (R=ethyl, R'=methoxymethyl): The compound is prepared starting from 2d analogously to Example 6 (xi).

(xiv) (c) 3(R)-(2-Methoxyethyl)-oxymethyl-7-azido-5-oxo-heptanoic acid ethyl ester 3e (R=ethyl, R'=2-methoxyethyl-oxymethyl): The compound is prepared starting from 2e analogously to Example 6 (xi).

(xv) (d) (3R,5R)-7-Azido-3,5-dihydroxy-heptanoic acid ethyl ester 4a (R=ethyl, R' and R" each=H): 0.28 g of the ketoazide 3b is dissolved in 2 ml of dry THF. A mixture of 2.5 ml of dry methanol and 9.5 ml of dry THF is introduced into a reaction vessel under an argon atmosphere at room temperature, and 1.4 ml of triethylborane are added. The mixture is stirred for 1 h at room temperature and then cooled to −65° C. The starting material is then added dropwise to the resulting solution within a period of 30 min. At −65° C., a total of 0.054 g of sodium borohydride is then added in portions and stirring is continued for a further 1 h at −65° C. The reaction mixture is brought to room temperature, diluted with ethyl acetate and extracted with 5% ammonium chloride solution. The organic phase is separated and dried over magnesium sulfate. After removal of the solvent, the residue is evaporated a further 5× with 40 ml of methanol and purified by chromatography over silica gel. 0.20 g of oily diol 4a is obtained: $^1$H-NMR (D$_2$O): 1.25 (t, 3H); 1.56 (m, 2H); 1.68 (m, 2H); 2.46 (d, 2H); 3.34 (m, 2H); 3.97 (m, 1H); 4.14 (q, 2H); 4.25 (m, 1H).

(xvi) (Conversion according to (d)) (3R,5R)-7-Azido-3,5-(2',2'-isopropylidene-dioxy)heptanoic acid ethyl ester 4b (R=ethyl, R', R"=together isopropylidene): 0.50 g of the compound 4a is dissolved in 1 ml of absolute THF, and at room temperature 0.25 g of dimethoxypropane and 0.01 g of toluenesulfonic acid are added. After 2.5 h, the reaction mixture is diluted with ethyl acetate and extracted in succession with saturated sodium chloride solution, saturated sodium hydrogen carbonate solution and saturated sodium chloride solution. After removal of the solvent, 0.50 g of product 4b is obtained: $^1$H-NMR (CDCl$_3$): 1.19 (t, 1H); 1.25 (t, 3H); 1.36 (s, 3H); 1.45 (s, 3H); 1.58 (dt, 1H); 1.70 (m, 2H); 2.32 (m, 2H); 2.51 (m, 2H); 3.38 (m, 2H); 4.00 (m, 1H); 4.14 (dq, 2H); 4.31 (m, 1H).

(xvii) (Conversion according to (e)) (3R,5R)-7-Amino-3,5-(2',2'-isopropylidenedioxy)heptanoic acid ethyl ester 5a (R=ethyl, R', R"=together isopropylidene): 10 g of the compound 4b are dissolved in 80 ml of ethanol; 500 mg of 5% palladium on carbon are added and the mixture is hydrogenated in an autoclave at 10 bar hydrogen pressure and temperatures of from 20 to 30° C. After about 1 h, the catalyst is filtered off and the mother liquor is concentrated in vacuo. 8.4 g of a brownish-green oil, the title compound, are obtained: 1H-NMR (CDCl$_3$): 1.26 (t, 3H); 1.35 (s, 3H); 1.44 (s, 3H); 1.55 (m, 2H); 1.69 (m, 2H); 2.36 (dd, 1H); 2.51 (dd, 1H); 2.90 (t, 2H); 3.86 (br s, NH); 4.00 (dddd, 1H); 4.13 (q, 2H); 4.29 (dddd, 1H).

(xviii) (Conversion according to (c*)) 3(R)-Hydroxy-5-oxo-hept-6-enoic acid ethyl ester 6f (R=ethyl, R'=H, Y=H): 11.6 g of crude acetylated olefin 6c are dissolved in 55 ml of ethanol and 200 ml of potassium dihydrogen phosphate buffer (0.05M, pH 7), and 0.05 g of esterase (PLE; Boehringer Mannheim) is added. The pH is maintained at a constant value using a pH stat and 0.5M sodium hydroxide solution and the reaction is purified by chromatography with silica gel after the theoretical amount of base has been consumed. 3.1 g of deacetylated olefin 6f are obtained: $^1$H-NMR (CDCl$_3$): 1.22 (t, 3H); 2.50 (d, 2H); 2.79 (m, 2H); 2.81 (m, 2H); 4.13 (q, 2H); 4.47 (m, 1H); 5.85 (dd, 1H); 6.25 (m, 2H).

(xix) (c') (3R,5R)-Dihydroxy-hept-6-enoic acid ethyl ester 7a (R=ethyl, R'=H, R"=H, Y=H)

2.60 g of the ketoolefin 6d are dissolved in 20 ml of dry THF. A mixture of 25 ml of dry methanol and 80 ml of dry THF is introduced into a reaction vessel under an argon atmosphere at room temperature, and 14.00 ml of triethylborane are added. The reaction mixture is stirred at room temperature for 1 h and then cooled to −65° C. The starting material is added dropwise to the resulting solution within a period of 30 min. At −65° C., a total of 0.58 g of sodium borohydride is then added in portions and stirring is continued for a further 1 h at −65° C. The reaction mixture is brought to room temperature, diluted with ethyl acetate and extracted with 5% ammonium chloride solution. The organic phase is separated and dried over magnesium sulfate. After removal of the solvent, the residue is evaporated a further 5× with 40 ml of methanol and purified by chromatography over silica gel. 1.80 g of oily diol 7a are obtained: $^1$H-NMR (CDCl$_3$): 1.21 (t, 3H), 1.61 (m, 2H); 2.44 (m, 2H); 3.60 (d broad, OH); 3.92 (d broad, OH); 4.10 (q, 2H); 4.23 (m, 1H); 4.33 (m, 1H); 5.03 (dt, 1H); 5.19 (dt, 1H); 5.79 (ddd, 2H).

(xx) (c') (3R,5S)-3,5-(2',2'-Isopropylidenedioxy)-hept-6-enoic acid ethyl ester 7b (R=tert-butyl, R' and R"=isopropylidene, Y=H): The compound is prepared in accordance with one of the processes described hereinabove and hereinbelow.

(xxi) (d') (3R,5R)-3,5-(2',2'-Isopropylidenedioxy)-6-oxo-hexanoic acid tert-butyl ester 8a (R=tert-butyl, R' and R"=isopropylidene): 500 mg of compound 7b (R=tert-butyl, R' and R"=isopropylidene, Y=H) are dissolved in 30 ml of methylene chloride and cooled to −78° C. Ozone is passed through the solution until the solution becomes pale blue. Flushing with oxygen is carried out for 5 min before a solution of 500 mg of triphenylphosphine in 5 ml of methylene chloride is added. The mixture is stirred at room temperature for 1 h and then concentrated by evaporation. The product is purified by means of flash chromatography, yielding 500 mg (99%) of the aldehyde 8a in the form of colourless crystals: $^1$H-NMR (CDCl$_3$): 1.24-1.41 (m, 1H); 1.41 (s, 2H); 1.45 (s, 3H); 1.76-1.82 (m, 1H); 2.31 (dd, J=15.1, 6.3, 1H); 2.42 (dd, J=15.1, 7.0, 1H); 4.25-4.34 (m, 2H); 9.45 (s, 1H).

(xxii) (e') (3R,5S)-7-Iodo-3,5-(2',2'-isopropylidenedioxy)-hept-6-enoic acid tert-butyl ester 9a (R=tert-butyl, R' and R"=isopropylidene): In a 100 ml two-necked flask, 2.83 g of dry CrCl$_2$ are suspended under argon in 36 ml of absolute THF and cooled to 0° C. A solution of compound 8a (990 mg) and 2.26 g of iodoform (CHI$_3$) in 18 ml of THF is added dropwise to the resulting suspension. The mixture is stirred for 16 h at room temperature and then poured into 70 ml of water and extracted with ether. The combined organic phases are washed with saturated sodium chloride solution and dried over sodium sulfate. After purification by column chromatography, 470 mg (32%) of the vinyl iodide 9a are obtained in the form of a yellow oil. The compound consists of 70% E- and 30% Z-isomer. $^1$H-NMR (CDCl$_3$): 1.21-1.39 (m, 1H); 1.40 (s, ca. 3H); 1.44 (s, 6.3H); 1.45 (s, ca. 3H); 1.46 (s, 2.7H); 1.53 (s, 0.3H); 1.56-1.78 (m, 1H); 2.29 (dd, J=15.4, 6.3, 0.7H); 2.32 (dd, J=15.0, 6.2, 0.3H); 2.44 (dd, J=15.3, 7.1, 1H); 4.21-4.38 (m, ca. 2H); 6.23 (dd, J=7.3, 7.3, 0.3H, Z); 6.34 (dd, J=7.9, 0.9, 0.3H, Z); 6.30 (dd, J=14.7, 0.9, 0.7H, E); 6.52 (dd, J=14.7, 5.6, 0.7H, E).

(xxiii) (b) 3(R)-7-Chloro-3-methoxyacetoxy-5-oxo-heptanoic acid ethyl ester 2f (R=ethyl, R'=methoxyacetyl, X=Cl, Y=H): 108.3 g of acid chloride 1c are dissolved in 60 ml of dry ethylene chloride and at 0° C. added dropwise in the course of 1 h to 156.0 g of aluminium trichloride in 500 ml of dry ethylene chloride, a slight rise in temperature being observed. Dry ethylene gas is passed through the clear solution, the temperature rising to about 4-10° C. When the absorption of gas has ceased, the mixture is poured into ice-cold saturated sodium chloride solution and extracted with ethyl acetate. The organic phase is washed twice more with saturated sodium chloride solution and dried over magnesium sulfate. 112.5 g of 2f are obtained in the form of an orange-yellow oil: $^1$H-NMR (CDCl$_3$): 1.25 (t, 3H); 2.70 (m, 2H); 2.90 (m, 2H); 3.41 (s, 3H); 3.72 (t, 2H); 3.97 (s, 2H); 4.13 (q, 2H); 5.62 (m, 1H).

(xxiv) (b) 3(R)-7-Chloro-3-hydroxy-5-oxo-heptanoic acid ethyl ester 2b (R=ethyl, R'=H, X=Cl, Y=H) (alternative synthesis): 20 g of crude 3(R)-7-chloro-3-methoxyacetoxy-5-oxo-heptanoic acid ethyl ester 2f are dissolved analogously to the acetyl derivative 2a (see Example 6 (ii)) in 400 ml of water; 1 ml of technical grade PLE (Roche) is added and the pH is maintained at 7 using a pH stat and 0.5N sodium hydrogen carbonate solution. When the theoretical amount of base has been consumed, the reaction mixture is washed repeatedly with hexane, and the product is then extracted from the aqueous phase with ethyl acetate, and the ethyl acetate phase is then washed with sodium chloride solution. After removal of the solvent, 9.4 g of the chlorine compound 2b remain behind in the form of a colourless liquid having spectroscopic data identical to those above.

(xxv) (c") (3R,5R)-7-Chloro-3,5-dihydroxy-heptanoic acid ethyl ester 10a (R=ethyl, R'=H, R"=H, X=Cl, Y=H): 38 ml (1M solution in THF) of triethylborane are introduced into 75 ml of dry tetrahydrofuran and 55 ml of dry methanol under an argon atmosphere at room temperature. The reaction mixture is stirred for 1 h at room temperature and then cooled to −65° C. 7.77 g of 2b, dissolved in THF, are then added dropwise to the resulting solution in the course of 30 min. At −65° C., a total of 1.45 g of sodium borohydride are then added in portions and stirring is continued for a further 1 h at −65° C. The reaction mixture is cautiously treated with 1N hydrochloric acid at −65° C. and brought to room temperature, diluted with ethyl acetate and extracted with saturated sodium chloride solution. The organic phase is separated off and dried over magnesium sulfate. After removal of the solvent, the residue is taken up in 120 ml of THF and at 0° C. cautiously oxidised with 12 ml of 35% hydrogen peroxide solution. The reaction mixture is diluted with ethyl acetate and extracted with saturated sodium chloride solution, and the organic phase is dried over magnesium sulfate. After filtration and removal of the solvent, an oil remains behind which is advantageously stirred with methanol in silica gel. 7.0 g of oily diol 10 are obtained after filtration and evaporation of the solvent: $^1$H-NMR (CD$_3$OD): 1.25 (t, 3H); 1.65 (m, 2H); 1.89 (m, 2H); 2.48 (d, 2H); 3.64 (m, 2H); 3.95 (m, 1H); 4.14 (q, 2H); 4.20 (m, 1H). This material is used directly in the next step.

An alternative method for the diaseroselective reduction of 2b to 10 is the heterogeneous reduction of 2b with hydrogen in the presence of magnesium acetate with platinium on carbon.

(xxvi) (c''') (3R,5R)-7-Chloro-3,5-(2',2'-isopropylidene-dioxy)-heptanoic acid ethyl ester 10b (R=ethyl, R' and R" together=isopropylidene=H, X=Cl, Y=H): 6.5 g of diol 10a are dissolved in 12.3 ml of dimethoxypropane, and 0.3 g of toluenesulfonic acid is added. After 4.5 h at about 40° C., the reaction mixture is diluted with ethyl acetate and extracted in succession with saturated sodium chloride solution, saturated sodium hydrogen carbonate solution and saturated sodium chloride solution. After removal of the solvent, 5.3 g of 10b are obtained: $^1$H-NMR (CDCl$_3$): 1.18 (t, 1H), 1.23 (t, 3H); 1.34 (s, 3H); 1.44 (s, 3H); 1.57 (dt, 1H); 1.85 (m, 2H); 2.43 (m, 2H); 3.59 (m, 2H); 4.11 (m, 3H); 4.30 (m, 1H).

(xxvii) (d''') (3R,5R)-7-Azido-3,5-(2',2'-isopropylidene-dioxy)heptanoic acid ethyl ester 4b (R=ethyl, R', R"=together isopropylidene) (alternative method): 4.5 g of chloride 10b are dissolved in 8 ml of dimethylformamide, and 1.20 g of sodium azide are added. The mixture is stirred at 55° C. until the reaction is complete, then diluted with ethyl acetate and extracted in succession with water and saturated sodium chloride solution. After evaporation of the solvent, 4.3 g of azide are obtained. The NMR data correspond to those indicated above for 4b.

Example 8

Further Use of Compound 5 from Reaction Scheme 11

For the preparation of atorvastatin, a compound 5 is reacted with a compound of formula 17

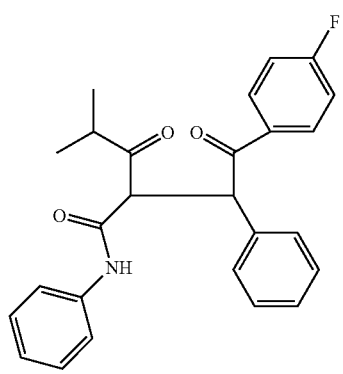

17 analogously to the conditions described in WO 89/07598 for the reaction between that compound and a compound of formula H$_2$N—CH$_2$CH$_2$—CH(OR$_{10}$)(OR$_{11}$), wherein R$_{10}$ and R$_{11}$ are alkyl having up to 8 carbon atoms or together are 1,2-(1-methyl)ethylidene, 1,2-ethylidene or 1,3-propylidene. Subsequent removal of protecting groups and, if necessary, opening of the lactone ring yields atorvastatin.

Example 9

Preparation of Cerivastatin Using the Aldehyde 8

For the preparation of cerivastatin, a compound 8 is reacted with a compound of formula 18

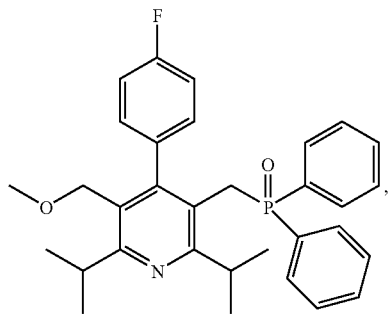

18 analogously to the conditions described in WO 00/49014 for the reaction between Ar—CH$_2$P(=O)(Ph)$_2$ (Ar=unsubstituted or substituted heterocyclyl or unsubstituted or substituted aryl, such as phenyl, etc.; Ph phenyl) and the compound 8. Subsequent removal of protecting groups and opening of the lactone ring yields cerivastatin.

Example 10

Suzuki Coupling with Compounds of Formula VIII

A compound 9 can be combined with the complementary aryl radicals by C—C linking under the conditions of a modified Suzuki coupling and thus, for example, after additional protecting group removal, itavastatin can be prepared.

What is claimed is:

1. A compound of formula I

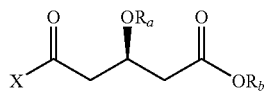

(I)

wherein X is halogen, acyloxy, activated hydrocarbyloxy, activated hydrocarbylthio or —N(CH$_3$)OCH$_3$, R$_a$ is a hydroxy-protecting group selected from the group consisting of lower alkoxy-lower alkanoyl, lower alkoxymethyl, and lower alkoxyethoxymethyl, and R$_b$ is a carboxy-protecting group.

2. A compound of formula I according to claim 1 wherein X is halogen, R$_a$ is lower alkoxy-lower alkanoyl, lower alkoxymethyl or lower alkoxyethoxymethyl and R$_b$ is lower alkyl.

3. A compound of formula I according to claim 2, selected from the following compounds: monoethyl-3(S)-methoxyacetoxyglutaric acid chloride or bromide, monoethyl-3(S)-methoxymethoxyglutaric acid chloride or bromide and monoethyl-3(S)-2-methoxyethoxymethoxyglutaric acid chloride or bromide.

\* \* \* \* \*